US011232577B2

(12) United States Patent
Zilberstien et al.

(10) Patent No.: US 11,232,577 B2
(45) Date of Patent: Jan. 25, 2022

(54) SYSTEMS AND METHODS FOR MEDICAL IMAGE REGISTRATION

(71) Applicant: Spectrum Dynamics Medical Limited, Road Town (VG)

(72) Inventors: Yoel Zilberstien, Herzlia (IL); Nathaniel Roth, Tel-Aviv (IL)

(73) Assignee: Spectrum Dynamics Medical Limited, Road Town (VG)

( * ) Notice: Subject to any disclaimer, the term of this patent is extended or adjusted under 35 U.S.C. 154(b) by 205 days.

(21) Appl. No.: 15/546,377

(22) PCT Filed: Jan. 26, 2016

(86) PCT No.: PCT/IL2016/050083
§ 371 (c)(1),
(2) Date: Jul. 26, 2017

(87) PCT Pub. No.: WO2016/120869
PCT Pub. Date: Aug. 4, 2016

(65) Prior Publication Data
US 2018/0005388 A1    Jan. 4, 2018

Related U.S. Application Data

(60) Provisional application No. 62/107,575, filed on Jan. 26, 2015.

(51) Int. Cl.
*G06T 7/32* (2017.01)
*A61B 6/03* (2006.01)
(Continued)

(52) U.S. Cl.
CPC ............... *G06T 7/32* (2017.01); *A61B 6/032* (2013.01); *A61B 6/037* (2013.01); *A61B 6/503* (2013.01);
(Continued)

(58) Field of Classification Search
None
See application file for complete search history.

(56) References Cited

U.S. PATENT DOCUMENTS

2006/0239524 A1    10/2006  Desh et al.
2009/0175562 A1*   7/2009   Pan ..................... A61B 6/027
                                                  382/312
(Continued)

FOREIGN PATENT DOCUMENTS

WO    WO 2016/120869    8/2016

OTHER PUBLICATIONS

Communication Pursuant to Article 94(3) EPC dated Sep. 24, 2019 From the European Patent Office Re. Application No. 16706912.9. (4 Pages).
International Preliminary Report on Patentability dated Jan. 6, 2017 From the International Preliminary Examining Authority Re. Application No. PCT/IL2016/050083. (20 Pages).
(Continued)

*Primary Examiner* — Vikkram Bali

(57) ABSTRACT

There is provided a method for registration of intravital anatomical imaging modality image data and nuclear medicine image data of a patient's heart comprising: obtaining anatomical image data including a heart of a patient outputted by an anatomical intravital imaging modality; obtaining at least one nuclear medicine image data outputted by a nuclear medicine imaging modality, the nuclear medicine image data including the heart of the patient; identifying a segmentation of a network of vessels of the heart in the anatomical image data; identifying a contour of at least part of the heart in the nuclear medicine image data, the contour including at least one muscle wall border of the heart; correlating between the segmentation and the contour; registering the correlated segmentation and the correlated contour to form a registered image of the anatomical image data and the nuclear medicine image data; and providing the registered image for display.

21 Claims, 18 Drawing Sheets

(51) Int. Cl.
  *A61B 6/00*    (2006.01)
  *G06T 7/33*    (2017.01)
  *G06T 7/38*    (2017.01)
  *G06T 7/11*    (2017.01)
  *G06T 7/13*    (2017.01)
  *G06T 7/00*    (2017.01)

(52) U.S. Cl.
  CPC .......... *A61B 6/5211* (2013.01); *A61B 6/5217* (2013.01); *A61B 6/5229* (2013.01); *A61B 6/5235* (2013.01); *G06T 7/0014* (2013.01); *G06T 7/11* (2017.01); *G06T 7/13* (2017.01); *G06T 7/33* (2017.01); *G06T 7/344* (2017.01); *G06T 7/38* (2017.01); *G06T 2200/08* (2013.01); *G06T 2200/24* (2013.01); *G06T 2207/10016* (2013.01); *G06T 2207/10081* (2013.01); *G06T 2207/10084* (2013.01); *G06T 2207/10104* (2013.01); *G06T 2207/10108* (2013.01); *G06T 2207/10116* (2013.01); *G06T 2207/30048* (2013.01); *G06T 2207/30096* (2013.01); *G06T 2207/30104* (2013.01)

(56) References Cited

U.S. PATENT DOCUMENTS

| 2011/0001761 | A1 | 1/2011 | Sakuragi |
| 2012/0263368 | A1 | 10/2012 | Nakano et al. |
| 2013/0216481 | A1* | 8/2013 | Rosenmeier ....... A61K 49/0004 424/9.1 |
| 2014/0003688 | A1 | 1/2014 | Hansis |
| 2014/0249399 | A1 | 9/2014 | Sharma et al. |
| 2015/0257845 | A1* | 9/2015 | Gopalakrishna ....... A61B 6/503 600/424 |
| 2016/0000392 | A1* | 1/2016 | Wong Po Foo ....... A61B 6/463 600/424 |

OTHER PUBLICATIONS

International Search Report and the Written Opinion dated Jun. 7, 2016 From the International Searching Authority Re. Application No. PCT/IL2016/050083.

Office Action dated Nov. 19, 2020 From the Israel Patent Office Re. Application No. 253683 and Its Translation Into English. (6 Pages).

* cited by examiner

SYSTEMS AND METHODS FOR MEDICAL IMAGE REGISTRATION

RELATED APPLICATIONS

This application is a National Phase of PCT Patent Application No. PCT/IL2016/050083 having International filing date of Jan. 26, 2016, which claims the benefit of priority under 35 USC § 119(e) of U.S. Provisional Patent Application No. 62/107,575 filed on Jan. 26, 2015. The contents of the above applications are all incorporated by reference as if fully set forth herein in their entirety.

BACKGROUND

The present invention, in some embodiments thereof, relates to systems and methods for registration of medical images and, more specifically, but not exclusively, to systems and methods for registration of anatomical medical images and nuclear medicine (NM) images.

Different imaging modalities are available to assess heart function. Each modality is designed to measure different aspects of the health state of the heart.

Physicians analyze data from the different types of images to gain an overall picture of the health of the heart, in order to help with diagnosis of disease, and to aid in selecting treatment. Exemplary imaging procedures include a coronary catheterization and a myocardial perfusion scan.

The evaluation of the heart with coronary catheterization is based on injection of a radio-opaque contrast into the coronary arteries. X-ray images of the heart are acquired, detailing how the coronary arteries have filled up with the injected contrast.

Certain lesions of the coronary arteries may be diagnosed from the fluoroscopic images, for example, stenotic lesions within the arteries that restrict the flow of blood into the heart muscle.

The evaluation of the heart with a myocardial perfusion scan is based on injection of a radioactive tracer into the patient. Single photon emission computed tomography (SPECT) images are acquired by sensing the radiation emitted by the tracers inside the body. When the heart muscle is diseased, and/or the coronary arteries are obstructed, less blood flows into certain muscle regions of the heart, and less radiation is emitted relative to regions that receive sufficient blood flow. Functional aspects of the heart may be diagnosed based on the SPECT images.

SUMMARY

According to an aspect of some embodiments of the present invention there is provided a computer implemented method for registration of intravital anatomical imaging modality image data and nuclear medicine image data of a heart of a patient, comprising: obtaining at least one anatomical image data outputted by an anatomical intravital imaging modality, the at least one anatomical image data including a heart of a patient; obtaining at least one nuclear medicine image data outputted by a nuclear medicine imaging modality, the at least one nuclear medicine image data including the heart of the patient; identifying a segmentation of a network of vessels of the heart in the at least one anatomical image data; identifying a contour of at least part of the heart in the at least one nuclear medicine image data, the contour including at least one muscle wall border of the heart; correlating between the segmentation and the contour; registering the correlated segmentation and the correlated contour to form a registered image of the at least one anatomical image data and the at least one nuclear medicine image data; and providing the registered image for display.

Optionally, the method further comprises retrieving the at least one anatomical image from a sequence of images including at least one previous image; and identifying the segmentation of the at least one anatomical image based on at least one seed point derived from a previous segmentation of the at least one previous image from the sequence of images. Optionally, the sequence of images is selected based on a range of images including a first frame prior to injection of contrast material into the network of vessels, and including a last frame of the contrast enhanced network of vessels prior to washing away of the contrast material from the network of vessels.

Optionally, the range of images are automatically selected based on the first frame denoted by an initial rise in a parameter representing size of a connected segmented component in each image, and based on the last frame denoted by a fall from a plateau of the parameter. Alternatively or additionally, the identifying the segmentation of the network of vessels is performed for at least two of the images within the range of images, and the at least two of the images are correlated with the same at least one nuclear medicine image data. Alternatively or additionally, the method further comprises connecting unconnected segmented vessels to form a single connected segmented component when the unconnected segmented vessels have a distance from the single connected segmented component that is less than a predefined threshold, and wherein unconnected segmented vessels that have the distance larger than the predefined threshold are excluded. Optionally, the predefined threshold is selected to exclude noise from the single connected segmented component.

Optionally, the method further comprises identifying a manual user input or automatic input indicative of a stenotic lesion within a certain vessel of the network of segmented vessels of the registered image; identifying a manual user input or automatic input indicative of at least one end region of the certain vessel feeding the heart wall muscle of the registered image; and calculating at least one physiological parameter based on correlated nuclear medicine imaging data of the portion of the heart wall associated with the certain vessel. Optionally, the at least one physiological parameter is selected from the group consisting of: perfusion of heart muscle fed by the certain vessel, perfusion defect severity or extent for heart muscle fed by the certain vessel, stress flow based on the certain vessel, coronary flow reserve based on the certain vessel, and NIFFR score. Alternatively or additionally, the method further comprises calculating percent stenosis of the stenotic lesion based on data from the registered image.

Optionally, the method further comprises identifying at least one manual user input indicative of at least one un-segmented vessel based on the registered image; and adapting the registered image to include the at least one un-segmented vessel as part of the segmented vessel network, based on the at least one manual user input acting as at least one seed point grown towards the segmented vessel network.

Optionally, the method further comprises obtaining another at least one anatomical image including contrast in a lumen of a left ventricle of the heart, outputted by the anatomical intravital imaging modality; identifying at least one anatomical structure of the left ventricle in the another at least one anatomical image; correlating between the contour and the at least one anatomical structure of the left ventricle; and correlating between the contour and the segmented vessel network based on the correlation between the contour and the at least one anatomical structure of the left ventricle.

Optionally, the method further comprises identifying a segmentation of the left ventricle heart muscle wall in the at least one nuclear medicine image, and wherein identifying the contour comprises identifying the contour of the heart muscle wall of the left ventricle.

Optionally, the registering is based on a projection of a generic angiographic model of heart vessels onto a 2D plane corresponding to a plane of the anatomical image of the segmented vessel network.

Optionally, obtaining comprises obtaining at least two sets of the at least one anatomical image based on at least two different views of the anatomical intravital imaging modality relative to the patient, and further comprising registering between the at least two sets based on relative respective positions of the anatomical imaging modality during the at least two different views. Optionally, the method further comprises generating a three dimensional (3D) model of vessels based on the segmented vessels of the registered at least two sets; and correlating and registering the contour based on the 3D model. Alternatively or additionally, the first set of the at least two sets includes contrast injected into the left main coronary artery, and the second set of the at least two sets includes contrast injected into the right coronary artery.

Optionally, the method further comprises generating a mesh projection of the contour; generating an ellipsoid generally encompassing the segmented network of vessels; and correlating the mesh projection with the ellipsoid.

Optionally, the method further comprises identifying a silhouette of the heart wall border visualized in the at least one anatomical image data; correlating between the contour and the silhouette; and correlating between the contour and the segmentation based on the correlation between the contour and the silhouette.

Optionally, the correlating is guided by identified certain vessels of the segmented vessels having predefined anatomical locations along the contour of the heart.

Optionally, the method further comprises identifying a location of an apex of the heart within the at least one anatomical image; correlating between the contour and the apex; and correlating between the contour and the segmentation based on the correlation between the contour and the apex.

Optionally, the method further comprises identifying the network of vessels within the at least one anatomical image data; generating a vessel image based on the identified network of vessels; selecting at least one seed point for the segmentation based on the vessel image such that the at least one seed point is located within the identified network of vessels; creating a homogeneity map to identify homogenous regions in the at least one anatomical image data; and segmenting the at least one anatomical image data based on the homogeneity map, the at least one seed point and the at least one anatomical image based on growing the seed points within the at least one anatomical image guided by the homogeneity map.

Optionally, the method further comprises repeating the limitations of the method a plurality of times during a cardiac catheterization procedure.

Optionally, registering comprises constraining the segmented vessel network within the contour by performing at least one of rotation and scaling of the contour based on obtaining minimum values calculated from a predefined cost function.

Optionally, the method further comprises selecting an anchor point for the segmented vessels to lock the segmented vessels in two dimensions to prevent translation of the segmented vessels and to allow scaling based on motion along an imaginary line connecting the anchor point and a detector. Alternatively or additionally, the method further comprises assigning equal weights to the inside of the contour for calculation of the cost function.

According to an aspect of some embodiments of the present invention there is provided a computer implemented method for adapting a registration between intravital anatomical imaging modality image data and nuclear medicine image data of a heart of a patient, comprising: obtaining a registered image generated between intravital anatomical imaging modality image data and nuclear medicine image data of a heart of a patient, the registered image including a segmentation of a network of vessels of the heart; identifying at least one manual user input indicative of at least one un-segmented vessel within the registered image; and adapting the registered image to include the at least one un-segmented vessel as part of the segmented vessel network, based on the at least one manual user input acting as at least one seed point grown towards the segmented vessel network. Optionally, the method further comprises enhancing the segmented vessel network within the registered image, and displaying the registered image including the enhanced segmented vessels as part of a user interface for receiving the at least one manual user input. Alternatively or additionally, the at least one manual user input is indicative of respective visible ends of the at least one un-segmented vessel.

According to an aspect of some embodiments of the present invention there is provided a system for registration of intravital anatomical imaging modality image data and nuclear medicine image data of a heart of a patient, comprising: a central server comprising: an anatomical interface configured to obtain at least one anatomical image data outputted by an anatomical intravital imaging modality, the at least one anatomical image data including a heart of a patient; a nuclear medicine interface configured to obtain at least one nuclear medicine image data outputted by a nuclear medicine imaging modality, the at least one nuclear medicine image including the heart of the patient; a hardware processor; a memory in communication with the processor, the memory having stored thereon modules for instruction execution by the processor, including: a segmentation module configured to identify a segmentation of a network of vessels of the heart in the at least one anatomical image data; a nuclear medicine data processing module configured to identify a contour of at least part of the heart in the at least one nuclear medicine image, the contour including at least one muscle wall border of the heart; a correlation module configured to correlate between the segmentation and the contour; a registration module configured to register the correlated segmentation and the correlated contour to form a registered image; and an output interface configured to provide the registered image for display.

Optionally, the system further comprises a user interface module configured to: identify a manual user input applied to the displayed registered image, the user input indicative of at least one vessel of the segmented vessel network; and display a result of a calculation of at least one functional physiological parameter based on nuclear medicine data of the correlated heart wall associated with the at least one vessel. Optionally, the at least one functional physiological parameter is selected from the group consisting of: perfusion defect, stress flow, coronary flow reserve, and NIFFR score.

Optionally, the anatomical intravital imaging modality includes an x-ray based fluoroscopic imaging machine.

Optionally, the nuclear medicine imaging modality includes a D-SPECT machine.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
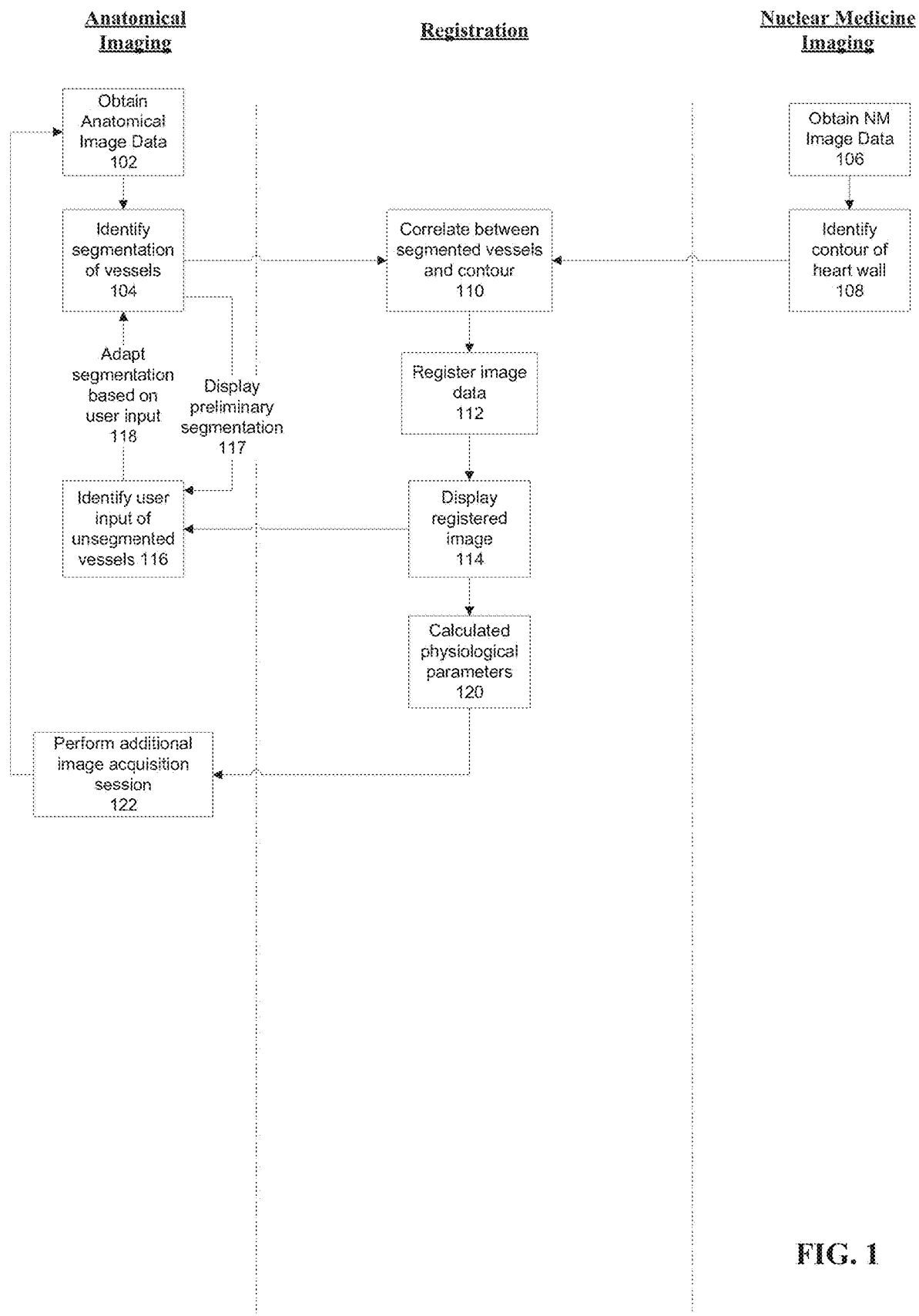
FIG. 1 is a flowchart of a computerized method for registration of medical images, in accordance with some embodiments of the present invention.

The present invention, in some embodiments thereof, relates to systems and methods for registration of medical images and, more specifically, but not exclusively, to systems and methods for registration of anatomical medical images and nuclear medicine images.

An aspect of some embodiments of the present invention relates to systems and/or methods for registration of intravital anatomical image data and nuclear medicine (NM) image data, including a heart (or portion thereof) of a patient. The registration is performed based on a correlation between segmented vessels (e.g., coronary vessels) of the heart derived from the anatomical image data and a contour of at least a portion of the heart wall derived from the NM image data. In this manner, functional imaging data represented by the NM images is registered with anatomical structural data represented by the anatomical images. The registered image may depict functional effects of structural lesions, for example, decrease in oxygen to the myocardium due to a stenosis in a certain coronary artery.

Optionally, physiological calculations are performed based on a manual user indication of a certain vessel on the registered image, using correlated NM data of the heart wall portion associated with the certain vessel. For example, the user marks the right coronary artery (which may include a stenotic lesion). Calculation of the coronary reserve flow is performed based on the NM data of the heart portion fed by the right coronary artery. An assessment of the effect of the stenotic lesion on heart function may be made based on the calculated values.

Optionally, the segmentation of the blood vessels is based on related anatomical images from sequence of images obtained during a period of time. The sequence of images depicts the pattern of contrast flow within the vessels of the heart, such a filling of the vessels with contrast and washing away of the contrast. Data obtained from images acquired before and/or after the current anatomical image being processed is used to segment the vessels within the current anatomical image. Segmented data from earlier images may serve as initial seed points for segmentation of the current image.

An aspect of some embodiments of the present invention relates to systems and/or methods for refining a registered image to include one or more additional vessels with the segmented vessel network, based on manual user input indicative of at least one un-segmented vessel in the registered image. The registered image is comprised from intravital anatomical image data and NM image data. The un-segmented vessel(s) is segmented and added to the segmented vessel network of the anatomical image. The anatomical image may be re-correlated and/or re-registered with the NM image data to generate an updated registered image. In this manner, the registration process is semi-automatic, using user provided input to improve the accuracy of the segmentation and/or registration.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
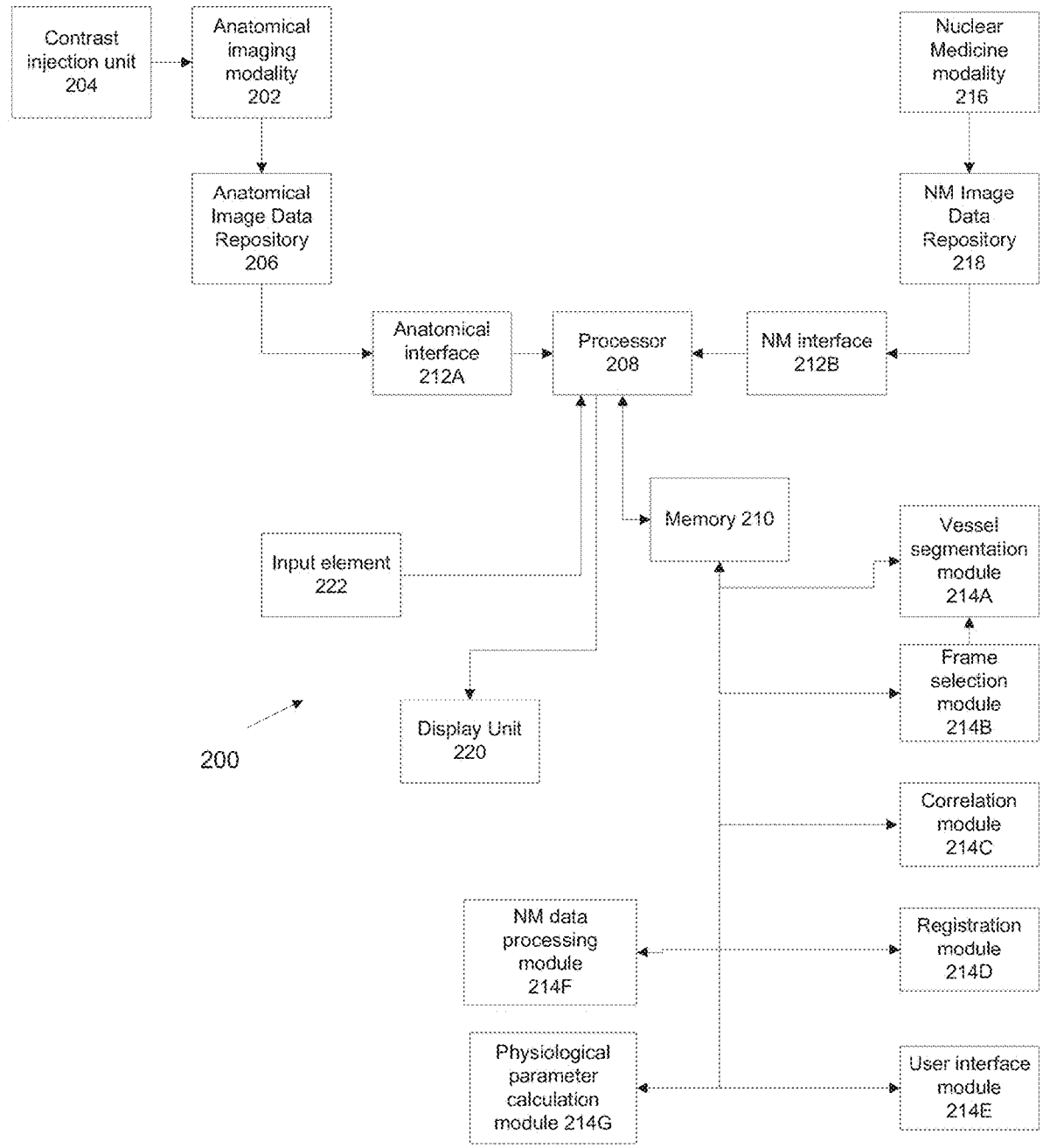
FIG. 2 is a block diagram of a system for registration of medical images, in accordance with some embodiments of the present invention.

Reference is now made to FIG. 1, which is a flowchart of a computer implemented method for registration of anatomical image data outputted by an intravital anatomical imaging modality and nuclear medicine image data outputted by a nuclear medicine imaging modality, in accordance with some embodiments of the present invention. Reference is also made to FIG. 2, which is a block diagram of a system for registration of anatomical image data and nuclear medicine image data, in accordance with some embodiments of the present invention. System 200 of FIG. 2 may be configured to execute the method based on FIG. 1.

The systems and/or methods described herein register two different types of images representing different aspects of the heart; anatomical image data representing structure of the heart, and functional image data representing function of the heart.

The registered image depicts the correlation between the structural features of the heart and functional performance of the heart. A healthcare working (e.g., interventional cardiologist, or surgeon) viewing the registered image may be able to determine the effect of certain lesions (e.g., stenosis) within vessels of the heart on the function of the heart muscle. Based on the registered image, the healthcare worker may select which lesion of which vessels to treat, and/or the manner of treatment. For example, certain lesions may appear structurally significant, but may actually not be associated with a significant decrease in functional performance of the heart (i.e., the heart may still receive enough oxygen in spite of the lesion, for example, the lesion looks worse than it actually is, and/or enough blood is provided to the muscle by other healthy vessels). In another example, certain lesions may appear structurally insignificant (e.g., small stenosis), but may actually be associated with a significant decrease in heart muscle function due to lack of sufficient blood flow.

The anatomical image data is registered with the NM image data based on correlation of features not visible in the corresponding image. The NM image depicts the heart wall muscle (i.e., generally the myocardium), which is difficult to visually define in the anatomical image data. The anatomical image data depicts heart vessels (e.g., coronary vessels), which are not visually depicted in the NM image.

At 102, one or more anatomical images are obtained. The anatomical image includes at least a portion of a heart of a patient. The anatomical image includes contrast enhanced lumens, for example, including the left main coronary artery and/or branches thereof, the right coronary artery and/or branches thereof, and/or the lumen of the left ventricle. Details of the processing of the images based on certain contrast enhanced lumens are described herein.

The anatomical image is outputted by an anatomical intravital imaging modality 202, for example, a fluoroscopy machine, a standard x-ray machine, a computerized tomography (CT) scanner, and a magnetic resonance imaging (MRI) scanner. A contrast injection unit 204 is configured to inject contrast into the lumens of the heart, for example, a catheter coupled to a syringe filled with contrast.

The anatomical image may be a two dimensional (2D) image comprised of pixels, or a three dimensional (3D) image comprised of voxels. As used herein, the term pixel may sometimes be interchanged with the term voxel. When several views of 2D images are obtained, the different views may be registered with each other, as described herein.

When imaging modality 202 obtains 2D images, two or more different views may be acquired, for example, separated by at least about 20 degrees, or at least about 30 degrees, or at least about 40 degrees. Modality 202 may include a single head camera with static or rotational acquisition ability. Modality 202 may include a dual head camera with static acquisition ability, the detectors separated to obtain the two or more different views. Each view may include a full artery tree with injected contrast (e.g., contrast injected into the ostium of the left main coronary artery or the right coronary artery from the aorta). Each view may include the left ventricle lumen having injected contrast. Each view may include images obtained over a full breathing cycle and/or a full heart beat cycle. Images may be taken when the patient is holding their breath.

The anatomical image may be stored in an anatomical image repository 206, located within modality 202, on a portable storage device, on a remote storage server (through a network connection), or on a local computer. The anatomical image may be provided to a hardware processor 208 coupled to a memory 210 having stored thereon one or more program modules having instructions for execution by processor 208. Processor 208 may be included within a computer, for example, within a desktop computer, a laptop computer, an imaging modality workstation, and a central server. Processor 208 may communicate with modality 202 by an anatomical interface 212A, for example, a network interface, a cable, a wireless link, and a portable storage device.

The anatomical image may be selected from a set of images selected from a time related sequence of images, for example, a video. The range of frames may be selected from the video to include a first frame taken prior to injection of contrast material into the network of vessels, and/or a last frame taken prior to the start of the contrast being washed away from the network of vessels.

The range of frames may be automatically selected. The first frame may be selected based on an initial rise in a parameter representing total contrast enhanced regions within the image, for example, a single connected component. The first frame may include an image of the catheter tip within the lumen about to be injected. The catheter may be shown full of contrast. The lumen may be shown without injected contrast. The last frame may be selected based on an initial drop in the parameter, after several frames during which the parameter has stabilized at a plateau. The stabilization of the parameter at the plateau is depicted by the vessels containing the contrast. The initial drop is depicted by the start of the contrast being washed away. The last frame may be acquired during the end of the diastolic phase, when the vessels are full of contrast.

Alternatively, the range of frames may be manually selected by the user. The user may manually specify the first frame and/or the last frame in the sequence, based on a visual inspection of the state of contrast within the vessels, as described herein.

Figure 3:
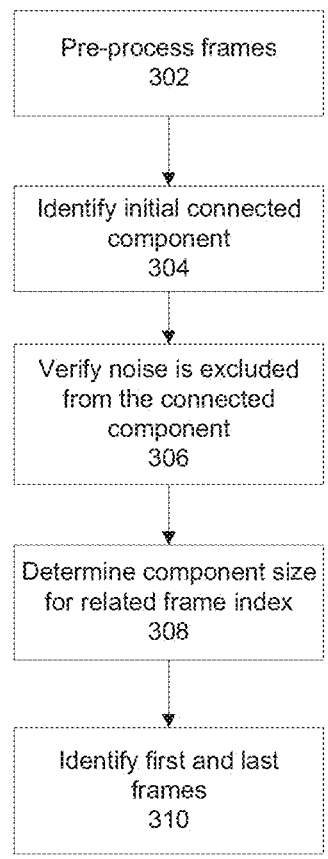
FIG. 3 is an exemplary computer implemented method for selecting anatomical frames for registration from a sequence of images, in accordance with some embodiments of the present invention.

Reference is now made to FIG. 3, which is a computer implemented method for automatic selection of certain frames, such as a range of frames, out of a sequence of time related frames for registration, in accordance with some embodiments of the present invention. The method identifies the first and the last frame in the sequence.

The method automatically selects the range of frames including a first frame just before or at the start of the contrast injection into the vessels, and a last frame when the contrast has stopped being injected (right before or at the start of washing away of the contrast). A frame selection module 214B (e.g., stored on memory 210) may be configured to perform the described method.

Optionally, at 302, each frame (or certain frames) in the sequence are pre-processed. The average video frame may be subtracted from each frame in the sequence. The subtraction may reduce noise and/or remove irrelevant background details.

At 304, an initial connected component is identified in one or more images, for example, in 1, 2, 3, or more images. The images containing the initial connected component serve as the initial baseline for selection of the first frame, as described herein. The images may be from the initial portion of the sequence.

Optionally, the initial connected component is a contrast loaded catheter. The contrast loaded catheter serves as a guide for locating the connected component providing the basis for segmentation of vessels. The catheter may be identified based on a segmentation of the image. The catheter may be identified as the largest connected component in the image. The catheter may be located in a position ready for injection of contrast into the target vessel, for example, in the aorta with the tip at the ostium of the left or right coronary artery network.

When contrast injection into the vessel network has started, subsequent identified single connected components include the regions within the vessel network containing contrast and the contrast loaded catheter.

The connected component may be identified, for example, based on the Fast Marching Method (FMM).

Optionally, at 306, a verification is performed to verify that noise was not incorrectly identified as a component in block 304. The verification is performed to verify that noise was excluded from the identified component. Exclusion of noise regions from the identified components prevents the noise from being segmented as part of the vessel network.

The distance between positions of the large single component and one or more additional nearby components (for possible inclusion within the large single component) may be calculated. When the distance is larger than a predetermined threshold, the distance may be measured on subsequent consecutive frames until the two components are identified having a distance below the threshold. The identified frame may be used as the starting point, based on the assumption that the two components having the distance between the threshold are not noise.

The predetermined threshold may be selected based on estimated lengths of stenotic lesions. In this regard, as distances smaller than the predetermined threshold may represent a stenosis, the method of joining the components across the unconnected distance is selected to join the components without visually affecting the stenosis, so that the stenosis remains visible to the user upon presentation. The section of the vessel filled with contrast past the stenosis is included as part of the single component region, and not incorrectly excluded as being noise.

At 308, the component size is determined for each of the frames (or certain frames). A search may be performed in a small predefined region around the largest identified component. All components within the region are identified. The total size of the identified components is calculated. The total size may be stored, for example, in an array linking the total size of the component with the index of the frame of the sequence.

The size of the identified components is expected to increase as a function of frame index number when injection of contrast has started.

At 310, the first and last frames are identified based on the relative value of the component size. The component size is expected to be stable for several frames until contrast injection begins (i.e., representing the contrast filled catheter). The first frame is selected when the component size rises (i.e., representing the start of contrast injection). The component size continues to rise as the vessels fill with contrast. The component size stabilizes at a plateau for several frames when the vessels are filled to capacity with contrast. The component size begins to drop when the contrast starts to leave the vessels (i.e., additional contrast is not injected). The last frame is selected when the component size begins to drop below the plateau. The component size continues to drop until the contrast has been washed away from the vessels. It is noted that the final component size (after the contrast has washed out) may be the same or different than the first component size (before contrast injection). When graphed, the component size as a function of frame index is expected to form a general trapezoidal shape. It is noted that the trapezoidal shape is a theoretical approximation, as noise and other variations in calculation of the component size deviate from the theoretical trapezoidal shape.

Based on the component size and/or identification of the contrast filled catheter, errors in vessel segmentation may be corrected. Portions of blood vessels or other tissue structures (without contrast) that are incorrectly segmented may be excluded. Segmented components that are smaller than the largest component may represent incorrect segmentation of tissues or vessels, and thereby excluded.

Segmented regions that are not connected to the largest connected region, or not connected to the contrast filled catheter may represent regions of incorrect segmentation of tissues or vessels, and thereby excluded. Segmented regions that are not directly connected to the largest connected region, or not directly connected to the contrast filled catheter, yet are close (i.e., less than the predetermined threshold) may represent correctly segmented regions. The unconnected segmented regions may be connected together with the largest segmented component, for example, based on the FMM method.

Figure 5:
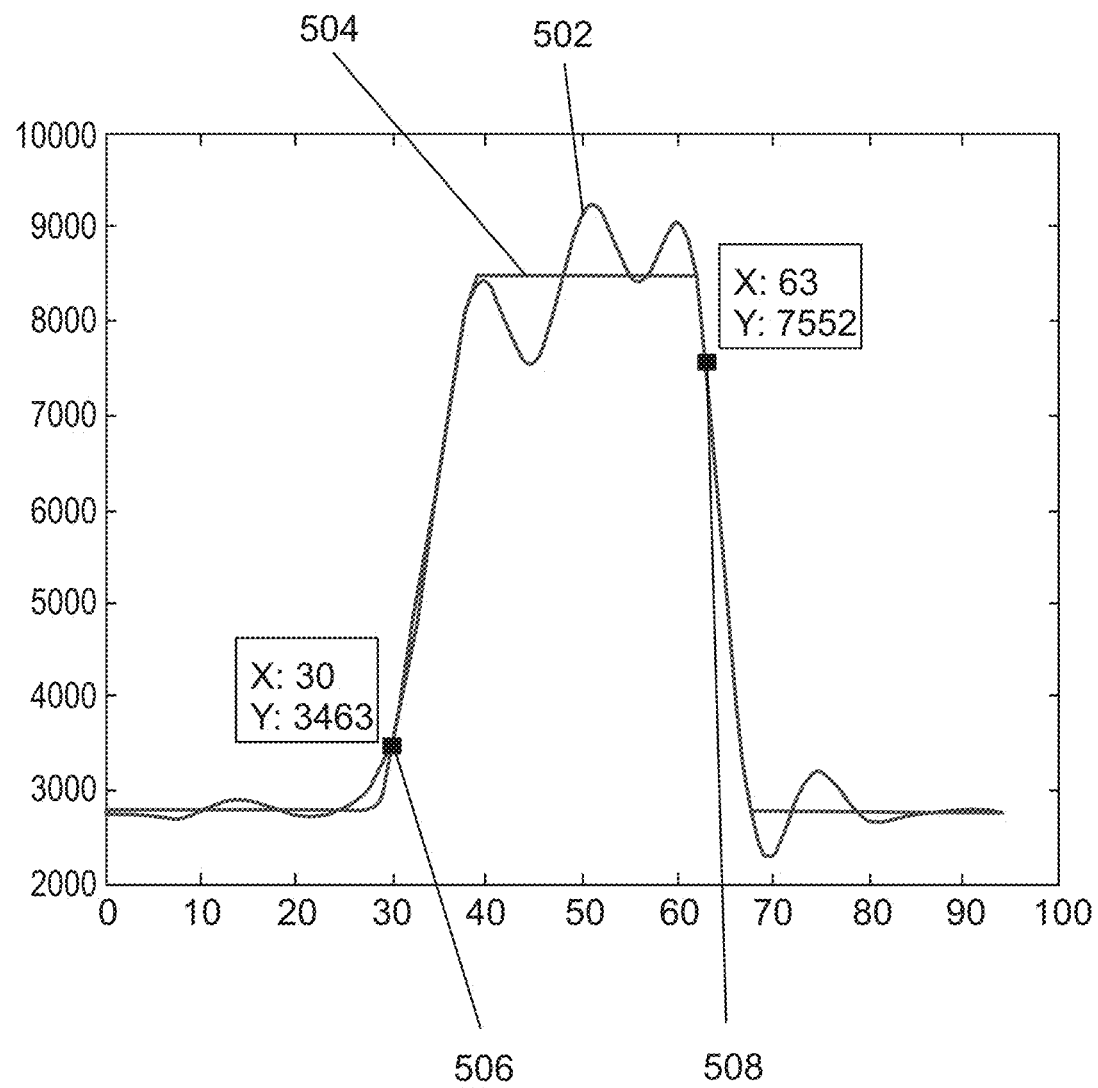
FIG. 5 is an example of a graph for automatic selection of first and last frames for segmentation of vessels, in accordance with some embodiments of the present invention.

Reference is now made to FIG. 5, which is an example of a graph depicting total component size (y-axis) as a function of a frame index number (x-axis) based on a sequence of acquired fluoroscopic images with contrast injection into the left main coronary artery network, in accordance with some embodiments of the present invention. The graph may be generated based on the method of FIG. 3, in particular block 310. Blue trace 502 follows the calculated values. Red trace 504 fits the general trapezoidal shape described with reference to block 310 to the calculated values. From the trapezoidal shape, a first frame 506 (index number 30) may be selected based on the first frame index number where the slope of the total component size begins to rise above the baseline (as described above). A last frame 508 (index number 63) may be selected based on the first frame index number where the slope of the total component size begins to fall below the plateau. Selection may be automatically performed by frame selection module 214B.

Figure 6:
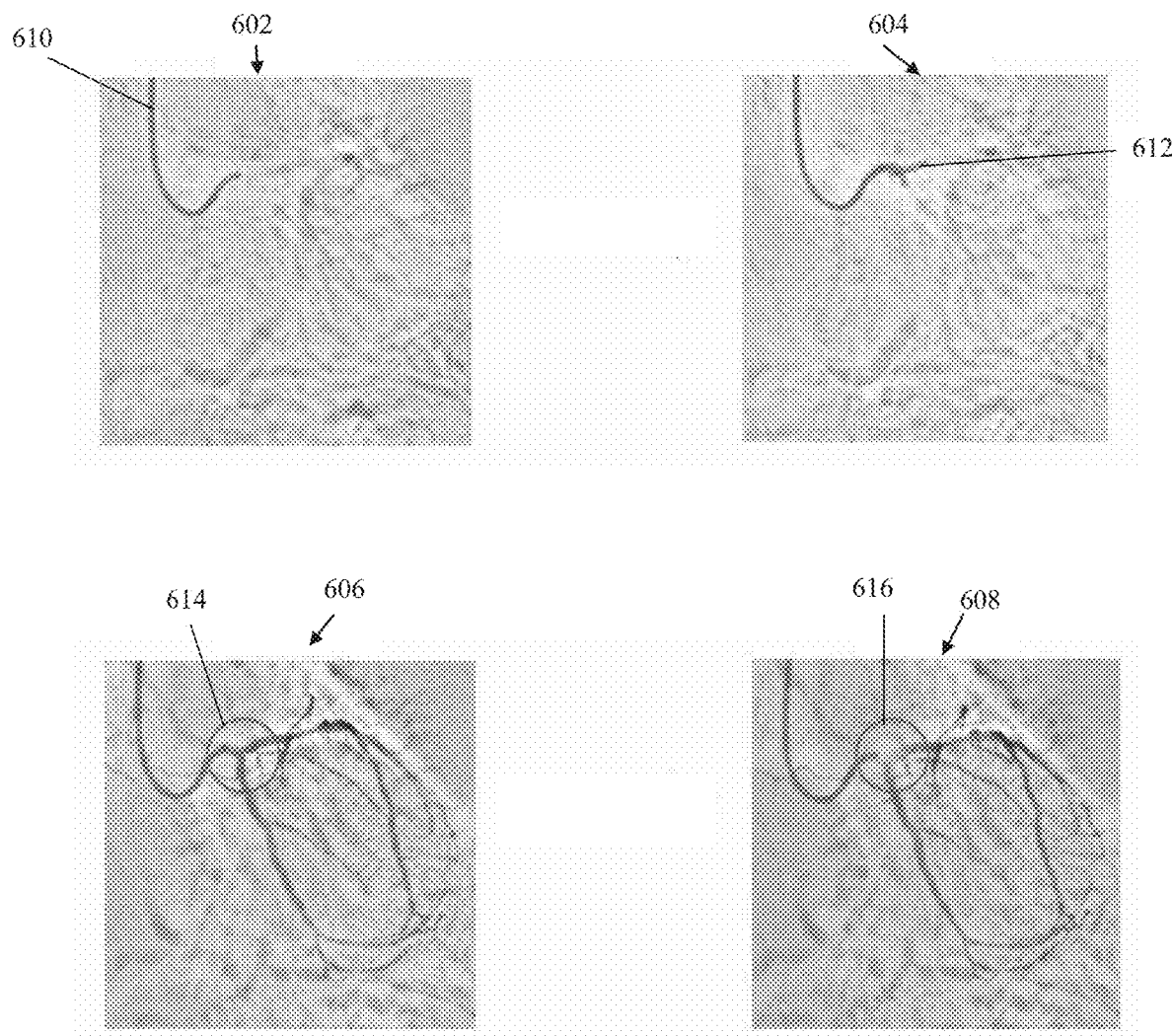
FIG. 6 includes anatomical images selected based on the graph of FIG. 5, in accordance with some embodiments of the present invention.

Reference is now made to FIG. 6, which depicts images selected based on the graph of FIG. 5, in accordance with some embodiments of the present invention. Image 602 depicts frame with index number 29, showing a contrast filled catheter 610 before injection. Image 604 depicts frame with index number 30, showing contrast filled catheter 610 after injection of contrast 612 has begun. Based on the graph, frame having index number 30 has been correctly identified as the first frame depicting the vessel network for segmentation. Image 606 depicts frame with index number 63, showing the presence of contrast within the vessel network in continuity with contrast filled catheter 610 (depicted within circle 614). Image 608 depicts frame with index number 64, showing the absence of contrast within the vessel network in proximity to catheter 610, after contrast injection has ended, and the process of contrast being washed away from the vessels as begun (depicted within circle 616). Based on the graph, frame index number 63 has been correctly identified as the last frame depicting the vessel network for segmentation.

Referring now back to FIG. 1, at 104, a segmentation of a network of vessels of the heart is identified in the anatomical image, optionally by vessel segmentation module 214A configured to segment the vessels as described herein. The segmentation of the vessels may be based on the visible contrast enhancement of the vessels.

Optionally, the segmentation is performed automatically, without requiring user intervention. User intervention may be provided after an initial image registration, to segmented additional missed vessels, as described herein.

Optionally, the segmentation is performed based on a selection of seed points depicting probable vessel locations. The seeds are grown within the vessel to define the region for segmentation. When multiple sequential frames are available, the segmented region may be grown from frame to frame. The previous frame segmentation may be used as initial seed points for the current frame. In this manner, small segmented areas are transitioned into the segmentation of the full network of vessels.

Figure 4:
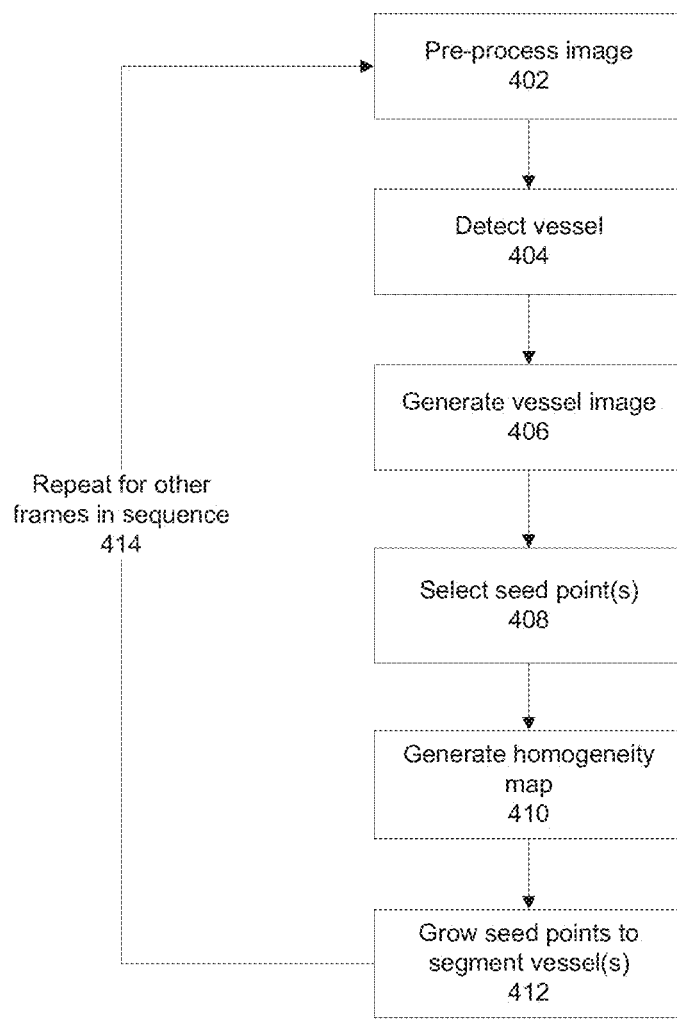
FIG. 4 is an exemplary computer implemented method for segmenting the anatomical image, in accordance with some embodiments of the present invention.

Reference is now made to FIG. 4, which is an exemplary computer implemented method of segmenting the network of vessels, in accordance with some embodiments of the present invention. Optionally, segmentation is performed for one or more frames obtained from the sequence of frames based on data from time related frames. Alternatively or additionally, segmentation is performed for individual frames independently of data from other frames (even when other frames are available).

Optionally, at 402, the image is pre-processed. When the image is obtained from a video of a sequence of time related images, an averaged video frame may be subtracted from the image to reduce noise and/or irrelevant background features. The image may be further processed by an Adaptive Histogram Equalization method to improve contrast. The image may be further processed by removal of objects of irrelevant size (e.g., larger or smaller than the expected size of the vessels) and/or enhancement of elements of desirable size (e.g., based on the expected size of the vessels).

At 404, the blood vessels, such as the coronary vessels and/or branches thereof, are detected, for example, by the method described by Frangi et al., described with reference to Alejandro F. Frangi, Wiro J. Niessen, Koen L. Vinc and Max A. Viergever (1998), "Multiscale Vessel Enhancement Filtering", Medical Image Computing and Computer-Assisted Intervention—MICCAI'98 Lecture Notes in Computer Science 1496/1998:130-137, incorporated herein by reference in its entirety. The Frangi filter is based on a multiscale approach to detecting tubes and ridges. The Frangi filter is based on eigenvalues of the Hessian matrix in scale space.

At 406, a vessel image is generated based on the detected blood vessels.

Optionally, the maximum response across different scales for every (or certain) pixel is obtained to product the vessel image.

Optionally, at 408, one or more seed points are selected based on the vessel image. The seed points are selected for region growing. Optionally, seed points located within the vessels are selected. Such seed points may decrease noise.

When the sequence of frames is available, frames prior (in time) to the current frame may be used for selection of the seed points. The seed points may be based on the vessel segmentation of the prior frame. Alternatively or additionally, the seed points may be manually selected by the user, for example, through an interface allowing the user to manually indicate one or more locations within vessels of the image.

Optionally, at 410, a homogeneity map is generated. Homogenous regions in the image are identified based on the homogeneity map. Edge points in the image are identified. The homogeneity map may be comprised of the local ratio between the local standard deviation and the local mean in the image.

At 412, the seed points are grown to segment the vessels. The region growing is performed on the image, based on the homogeneity map, the selected seed points and the enhanced image.

Optionally, at 414, blocks 402-412 are repeated for additional image frames in the sequence.

Referring now back to FIG. 1, at 106, nuclear medicine image data is obtained. The image data includes at least a portion of the heart of the patient, for example, the left ventricle. The image data may be collected as part of a heart imaging procedure, for example, a cardiac perfusion scan, at rest and/or with induced stress.

The NM image is outputted by a NM imaging modality 216, for example, a single photon emission computed tomography (SPECT) machine, a D-SPECT® machine available from Spectrum Dynamics Medical, a Biosensors International Group Company, and a positron emission tomography (PET) machine.

The anatomical image may be stored in a NM image repository 218, located within modality 202, on a portable storage device, on a remote storage server (through a network connection), or on a local computer. The NM image may be provided to processor 208, optionally through a NM interface 212B.

The anatomical image may be a two dimensional (2D) image comprised of pixels, or a three dimensional (3D) image comprised of voxels.

At 108, a contour of at least a part of the heart in the NM image is identified, optionally by a NM data processing module 214F configured to process NM image data as described herein. The contour includes one or more muscle borders of the heart, for example, the inside border (e.g., left ventricle), and/or the outer border.

Optionally, the contour is identified based on a segmentation of the left ventricle from the NM image. The left ventricle may be segmented, for example, based on intensity values. The left ventricle contains more muscle than other regions of the heart, and therefore receives a substantially larger volume of blood. Muscle of the left ventricle wall appears with higher intensity (representing higher function and/or higher blood volume) relative to other regions of the heart.

Alternatively, the contour is identified within the image, without segmentation of the left ventricle, for example, based on intensity values, based on predefined geometrical patterns, or other methods. The intensity of other regions of the heart may be sufficiently low so that segmentation of the left ventricles is not required.

Optionally, the center of the left ventricle and/or the orientation of the left ventricle is identified. The center and/or orientation may be identified for the identified contour, for example, by calculation of the geometrical center of the contour. The center and/or orientation of the contour may be used for correlation and/or segmentation with the segmented vessel network.

Figure 7:
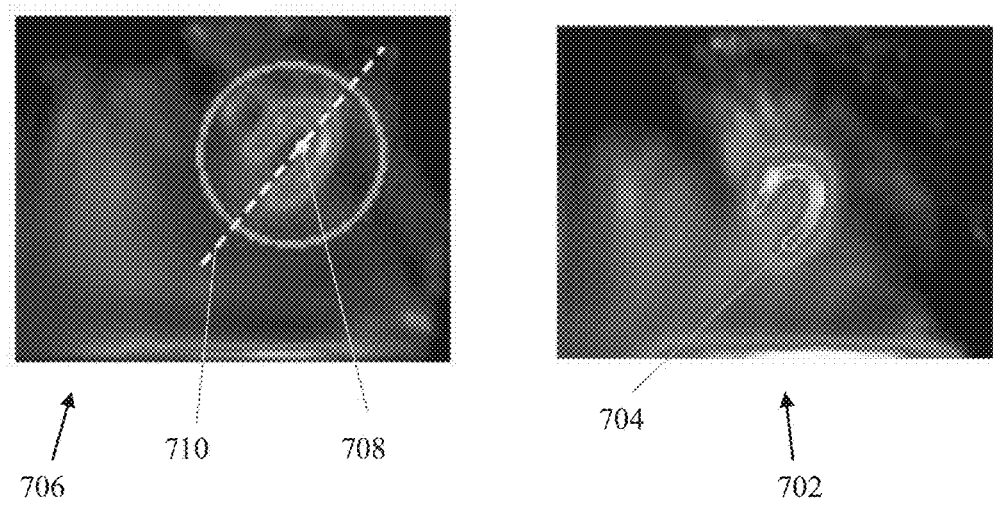
FIG. 7 includes examples of NM images depicting contour identification, in accordance with some embodiments of the present invention.

Reference is now made to FIG. 7, which includes examples of NM images of the heart of a patient obtained from a D-SPECT® imaging machine, depicting identification of the contour of the left ventricle, in accordance with some embodiments of the present invention. The left ventricle is depicted using a color code representing intensity values relative to levels of a radioactive isotope within the myocardium. The left ventricle is shown in particular, as blood supply to the muscle of the left ventricle is significantly higher than to the rest of the heart due to the large mass of left ventricle muscle as compared to the rest of the heart.

Image 702 depicts an outline of a contour 704 identified within the intensity image acquired from the left ventricle. Image 706 depicts a center 708 of the left ventricle, and an orientation line 710 representing the orientation of the contour and/or the left ventricle.

Referring now back to FIG. 1, at 110, the segmented vessels of the anatomical image are correlated with the contour of the heart wall of the NM image. Optionally, the correlation is performed by a correlation module 214C in communication with processor 208. Module 214C is configured to perform the correlation based on one or more methods described herein.

Correlation may be performed based on one method, or based on multiple methods. The multiple methods may be applied sequentially, in parallel, and/or iteratively, such as performing a first rough correlation, and then further refining the correlation to improve accuracy. Correlation may be performed in 2D and/or in 3D.

Optionally, the shape of the heart contour is estimated from the segmented vessel network, which is correlated with the contour of the NM image.

The NM image may include three dimensional data (e.g., as voxels), which is correlated with two dimensional data (e.g., as pixels) of the anatomical image (e.g., an x-ray image). Alternatively or additionally, the NM image includes 2D data which is correlated with 2D data of the anatomical image. Alternatively or additionally, the NM image includes 3D data which is correlated with 3D data of the anatomical image (e.g., a CT scan image). Alternatively or additionally, the NM image includes 2D data which is correlated with 2D data of the anatomical image.

It is noted that the same NM contour image may be correlated with different anatomical image frames, such as frames within a video.

The NM image and the anatomical image are acquired using different image modality devices, which may operate from different relative viewpoints and/or at different scales. As such, the anatomical image and/or the NM image may be translated, rotated and/or scaled to assist with the correlation, to change the size and/or orientation of the NM image to allow or improve correlation with the anatomical image. The changes in size and/or orientation may be performed automatically by a software module, and/or manually by the user visualizing the correlated results and using a user interface to make the adjustments.

Optionally, the correlation is based on correlation of a generated mesh (or other outline) projection of the NM heart wall contour with a generated ellipsoid selected to generally encompass the segmented network of vessels. The mesh and ellipsoid may provide a rough correlation, which may then be further refined based on other methods described herein, or provide the correlation basis for registration. The mesh may be selected based on a 2D slice of the NM left ventricle image depicting the LV lumen. The mesh may represent the contours of the left ventricle wall. The ellipsoid may be selected to encompass most of the vessels located within the left ventricle, and optionally excluding vessel regions located outside the left ventricle, such as the initial portions of the left main coronary artery next to the aorta. The ellipsoid may be selected to encompass the left main coronary artery from the main bifurcation. The ellipsoid may have a predefined size and/or diameter(s) based on expected size of the left ventricle, guided to position based on the location of the segmented vessels. The ellipsoid may be correlated on two different anatomical images obtained from two different views (as described herein).

Figure 8:
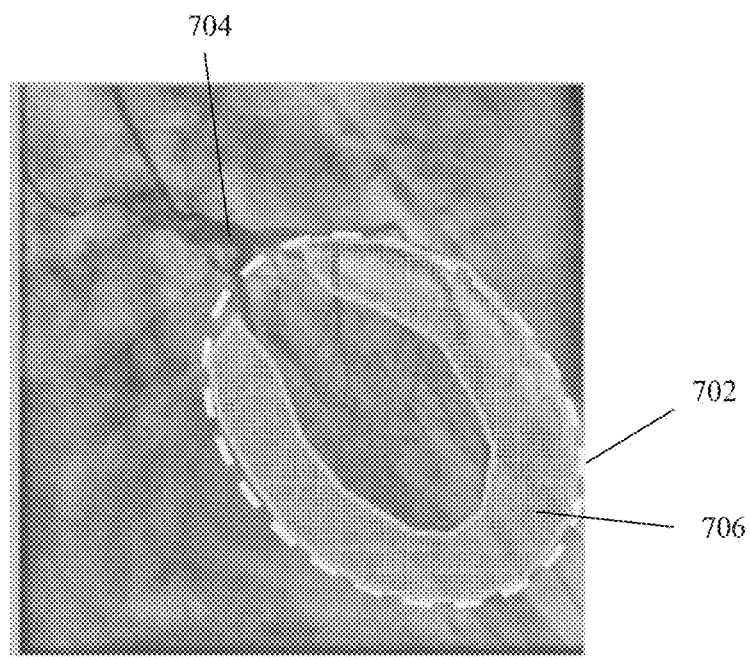
FIG. 8 is an image depicting correlation based on an ellipsoid and a contour mesh, in accordance with some embodiments of the present invention.

Reference is now made to FIG. 8, which is a fluoroscopic image having overlaid thereon a generated ellipsoid 702 encompassing a segmented vessel network 704, and a generated mesh 706 of the left ventricle heart wall contour correlated with ellipsoid 702, in accordance with some embodiments of the present invention.

Referring now back to FIG. 1, alternatively or additionally, the correlation is based on the anatomical structure of the left ventricle, obtained from one or more anatomical images. The correlation is based on anatomical images that include contrast in the lumen of the left ventricle. The left ventricle lumen may be identified in an image acquired at the end of the systolic phase (i.e., when the heart muscle is contracted) and/or at the end of the diastolic phase (i.e., when the heart muscle is relaxed), for example, the left ventricle lumen may be segmented from the image.

In such images, anatomical structures of the left ventricle may be identified and/or located, for example, the contour of the inner muscle wall, the base, the apex, angulations of the left ventricle, and/or the center of the left ventricle. The contour of the NM image may be correlated with the identified left ventricle structures. The NM contour may be correlated with the vessel network based on the correlation of the NM contour with the LV structures, for example, by a correlation between the vessel network with the correlated images that include contrast within the LV lumen. The correlation with the images that include the LV lumen may be a rough correlation, which guides a more accurate correlation based on the segmented vessels.

Figure 9:
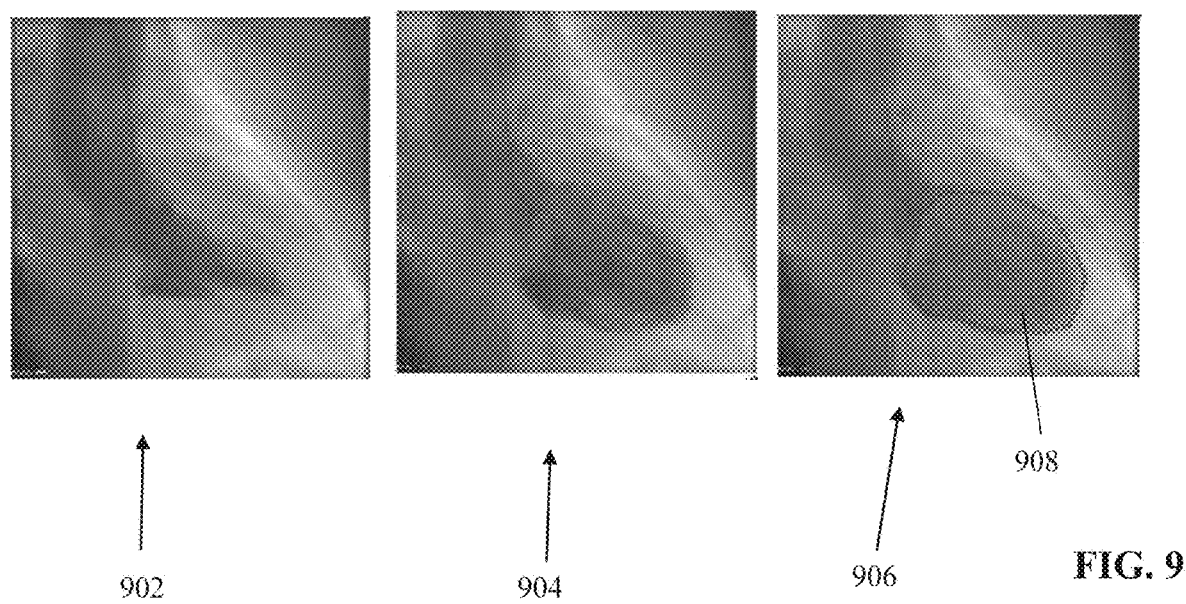
FIG. 9 includes images of the contrast filled left ventricle lumen for identification and/or localization of certain anatomical structures of the heart, in accordance with some embodiments of the present invention.

Reference is now made to FIG. 9, which depicts identification of anatomical structures of the left ventricle, in accordance with some embodiments of the present invention. Image 902 is a fluoroscopic image acquired during contrast injection into the lumen of the left ventricle at the end of the systolic phase. Image 904 is a fluoroscopic image acquired during contrast injection into the lumen of the left ventricle at the end of the diastolic phase. Image 906 depicts a segmentation 908 of the left ventricle. Certain anatomical structures of the heart may be identified and/or located based on segmented left ventricle 908, for example, the base, the apex, angulation of the left ventricle, and/or the center of the left ventricle.

Referring now back to FIG. 1, alternatively or additionally, the correlation is based on a myocardial silhouette visualized within the anatomical image. The myocardial silhouette may be identified and/or segmented from the anatomical image including the segmented vessels. The silhouette may be identified in another anatomical image taken from the same relative position of the sensor and table, such as after contrast has left the vessels, or before injection of contrast. The NM contour may be correlated with the myocardial silhouette as a rough correlation, to guide a more accurate correlation with the segmented vessels.

Alternatively or additionally, the correlation is based on an identified location of the heart apex (or other heart anatomical structure). The heart apex may be identified within the anatomical image based on the user manually positioning a tip of a catheter at the apex, for example, by segmentation of the catheter. The image depicting the catheter at the apex may be manually identified by the user, or automatically selected by a suitable software module. The anatomical heart apex may be correlated with the NM contour. The NM contour may be correlated with the segmented vessels based on the correlation with the apex. For example, the correlation with the heart apex provides a rough correlation for guiding a more accurate correlation of the NM contour with the segmented vessels.

Alternatively or additionally, the correlation is based on predefined locations of certain vessels of the segmented vessels within the heart. For example, the left circumflex (LCX) coronary artery is expected to run towards the lateral wall of the left ventricle, and around the basal plane. For example, the left anterior descending (LAD) coronary artery is expected to run down towards the apex of the heart.

The anatomical location of the certain vessels of the segmented vessels may guide the correlation with the NM contour of the heart wall. The certain vessels of the segmented vessels having predefined anatomical locations may be identified from the segmented network of vessels, for example, based on manual user input identifying the vessels, based on mapping to a predefined vessel model identifying the certain vessels, based on size, based on order of contrast filling, or based on other methods.

At 112, the correlated anatomical image and NM image are registered.

Registration of the images may be based on registration of the correlated segmented vessels and the correlated contour. Optionally, the registration is performed by a registration module 214D in communication with processor 208. Module 214D is configured to perform the registration based on one or more methods described herein. Registration may be performed based on one method, or based on multiple methods. The multiple methods may be applied sequentially, in parallel, and/or iteratively, such as performing a first rough segmentation, and then further refining the segmentation to improve accuracy. Registration may be performed in 2D and/or in 3D.

As described herein, some or all of the registration methods may sometimes be used for correlation (i.e., block 110), with or without the registration. For example, processing to help calculate coordinates of the segmented vessels may first be used to correlate with the NM contour, and then to calculate the registration.

Optionally, registration is based on the patient table position relative to the detector, which may be obtained from the respective imaging modality. Both the table position and the position of the detector (e.g., NM detector, x-ray detector) may be obtained for calculation of relative positions.

Optionally, registration is based on the obtained two or more different views of the anatomical images. The 3D location and/or orientation of the vessel network may be calculated based on the relative location of the vessels within each image of each view. The 3D location and/or orientation of the heart may be derived based on the calculated vessel network location and/or orientation. The NM image may be registered to the calculated 3D anatomical data.

Alternatively or additionally, registration (and/or correlation) is based on a projected generic angiographic model. The genetic angiographic model may be a 3D model (e.g., based on data from one or more other patients, and/or from an atlas), which is projected onto a 2D plane corresponding to the location and/or orientation of the 2D anatomical image of the segmented vessels. The similarity between the segmented vessel network and the projected 2D model is evaluated. Registration may be performed, for example, between the NM contour and the projected 2D model (as a first rough registration), which may be further corrected to the corresponding segmented vessel network. The 2D plane may be selected based on the corresponding view of the anatomical image, such as based on the relative table and/or sensor position.

Alternatively or additionally, a 3D vessel network segmentation is generated based on two or more views of the segmented vessel from respective 2D anatomical images. The respective 2D images are registered, to allow for generation of the 3D vessel network. The 3D vessel network is registered (and/or correlated) with the NM contour. Registration (and/or correlation) of the respective 2D image(s) may be calculated based on the registration of the 3D vessel network.

Alternatively or additionally, the NM contour is registered with one or more anatomical images depicting the right coronary artery (RCA). The image may include contrast injected into the RCA and branches thereof. The RCA and branches thereof may be segmented, as described herein. The registration of the NM contour with the images depicting the RCA may be based on the registered image(s) of the NM contour with the anatomical image depicting the left coronary artery based network of vessels. When images including the left coronary vessel network are registered with the NM contour, registration of the images including the RCA with the images including the left coronary artery also registers the images including the RCA with the same NM contour. As the images of the left and right vessel networks are registered with each other, once the image of the left vessel network are registered with the NM contour, the images of the right vessel network are also automatically registered with the same NM contour. The registration and/or correlation may be guided and/or further refined, for example, based on predefined anatomical relationships between vessels and the heart muscle wall (e.g., right coronary artery runs towards the inferior wall of the heart), and/or based on translation, rotation and/or scaling on the NM image (manually by the user and/or automatically by the software module).

Alternatively or additionally, registration is based on the method described with reference to FIG. 14, which is a flowchart of a computerized method for registration of the identified heart wall contour based on NM data and the segmented vessel network based on anatomical image data, in accordance with some embodiments of the present invention. The method is based on constraining the segmented vessels into the identified heart wall contour. The constraining is performed by one or more of: rotation, translation, and scaling of the heart wall contour and/or the segmented vessels. The constraining may be selected based on obtaining minimum values of a predefined cost function. An optimal registration may be achieved based on the cost function. The registration method provides, for example, a method for performing a heart catheterization procedure under fluoroscopic guidance and registration of the heart contour (obtained from NM data) directly onto the fluoroscopic images.

At 1402, the contour identified based on the NM image data is received.

Optionally, the contour is the contour of the left ventricle of the heart of the patient.

The segmented vessel network image data is received. The image may be of the segmented vessel network, or an image including the segmented vessel network may be received, such as an angiographic image including the vessels.

The contour and segmented vessels are optionally correlated as described with reference to block 110.

Optionally, at 1404, one or more anchor points are selected. Optionally, the anchor points are selected based on the image of the segmented vessel network.

Alternatively, the anchor points are selected based on the image of the contour.

Optionally, one anchor point is selected. The anchor point locks the image of the segmented vessel network and/or the contour in two dimensions, to prevent further translation during the registration. The third dimension along an imaginary line that connects the anchor point and the detector used to generate the image data remains unlocked, allowing freedom of movement along the imaginary line for scaling of the image. Additionally, freedom of rotational movement is allowed.

The anchor point may be selected manually by the user, for example, through a graphical user interface that allows the user to select the location of the anchor point on a displayed image of the segmented vessel network and/or the contour.

Alternatively or additionally, the anchor point may be automatically selected by a software module programmed to select the anchor point based on a set of rules.

The image may be translated for selection of the anchor point, with the certain translation locked based on the selected anchor point.

The anchor point may be selected, for example, along the left main coronary artery or other coronary vessels. The anchor point may be selected based on the view of the detector generating the anatomical image data, according to the vessel that the view is directed towards.

At 1406, one or two parameters are optimized for the NM image data of the identified contour: scaling (i.e., translation along the $3^{rd}$ dimension towards or away from the detector which results in image sizing), and/or rotation around the x-axis (or another axis, such as a longitudinal axis) of the patient.

The selection of one or both of the parameters is defined by a cost function based on the identified 3D outline contour of the NM image data. The cost function may be based on the contour of a projected 3D mesh model, for example, as shown and described with reference to FIG. 8.

The cost function is calculated based on a generated distance transform from the contour to the segmented vessel network. Equal weights may be assigned to the inside of the contour, to represent the fact that the inside of the left ventricle does not contain the segmented vessels (which are contained in the wall of the left ventricle contour). The equal weights represent that the distance from the contour wall (i.e., heart wall) to the segmented vessel network is significant, while distances from any location within the contour to the segmented vessel network are to be considered in the same manner. Data may be obtained from the NM data of the 3D model, without necessarily requiring data from the vessel graphs (i.e., depicting vessel contrast filing patterns as described herein), which may provide for faster and/or more efficient computation.

The distance may be calculated, for example, based on geometrical properties, for example, properties obtained from the segmented vessel network and/or from the mesh or other geometrical approximations of the contour. The distance may be calculated, for example, based on pixel intensity values representing the segmented vessel network and/or the contour.

The cost function may be calculated based on, for example, a least squares approach, a normalized correlation approach, or other methods.

At 1408, the registered data is provided as output of the computerized method.

The registered data may include common coordinates for the NM image data and the segmented vessel network and/or a combined registered image.

Figure 14:
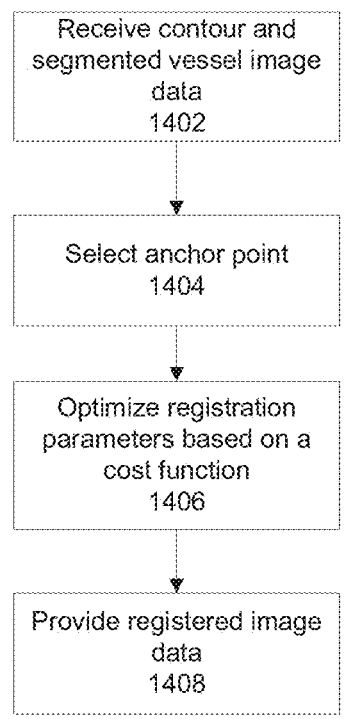
FIG. 14 is a flowchart of a computerized method for registration of the identified heart wall contour based on NM data and the segmented vessel network, in accordance with some embodiments of the present invention.
Figure 15A:
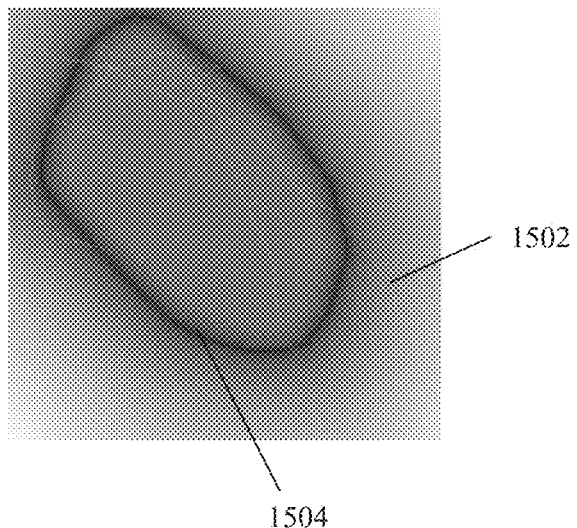
FIGS. 15A and 15B are images depicting registration based on the method of FIG. 14, in accordance with some embodiments of the present invention.
Figure 15B:
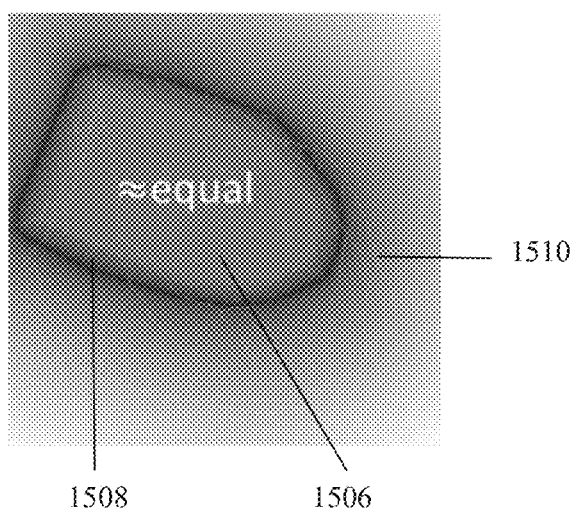

Reference is now made to FIGS. 15A and 15B, which depict image data registration based on the method of FIG. 14, in accordance with some embodiments of the present invention. FIG. 15A depicts registration between segmented vessels anatomical image data 1502 and left ventricle contour NM image data 1504. FIG. 15B depicts a region 1506 within left ventricle contour NM image data 1508 having equal weight for calculation of the cost function, and registration with segmented vessels 1510.

Reference is now made to FIGS. 16A-E, which depict calculation of the scaling parameter and the rotational parameter based on experimentally measured data, and registration of the image data, based on the method of FIG. 14, in accordance with some embodiments of the present invention. Values calculated based on the cost function are compared to experimentally determined values to illustrate the accuracy of calculation based on the cost function.

Figure 16B:
FIGS. 16A-E include graphs representing experimentally measured values of the scaling parameter and the rotational parameter, and images depicting registration of the image data based on the method of FIG. 14, in accordance with some embodiments of the present invention.
Figure 16A:
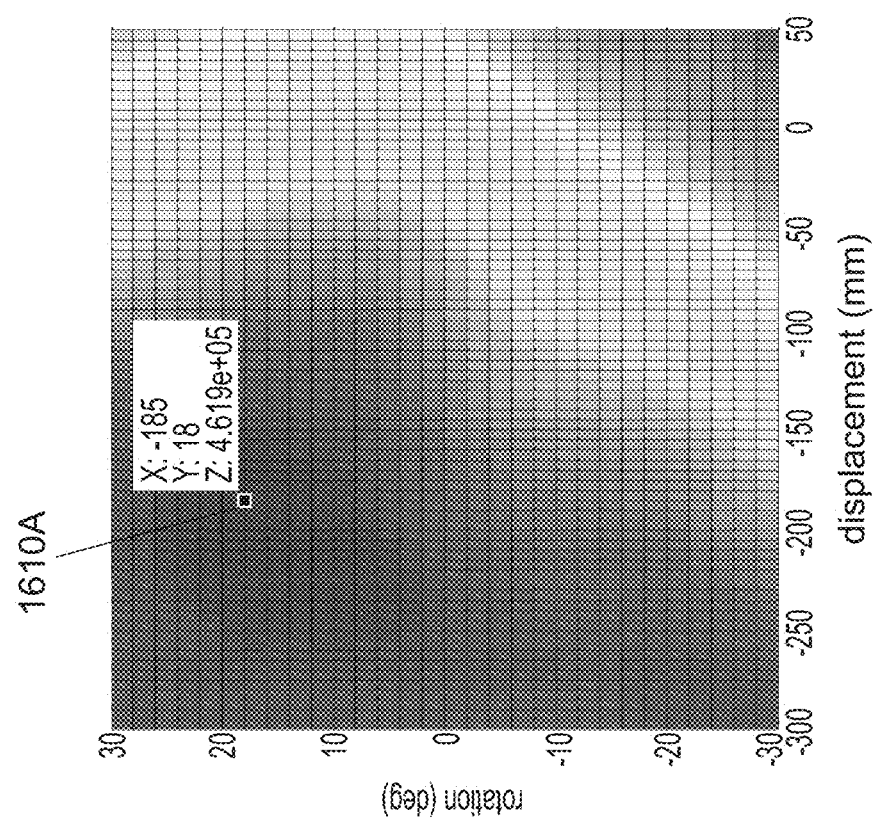
Figure 16D:
Figure 16C:
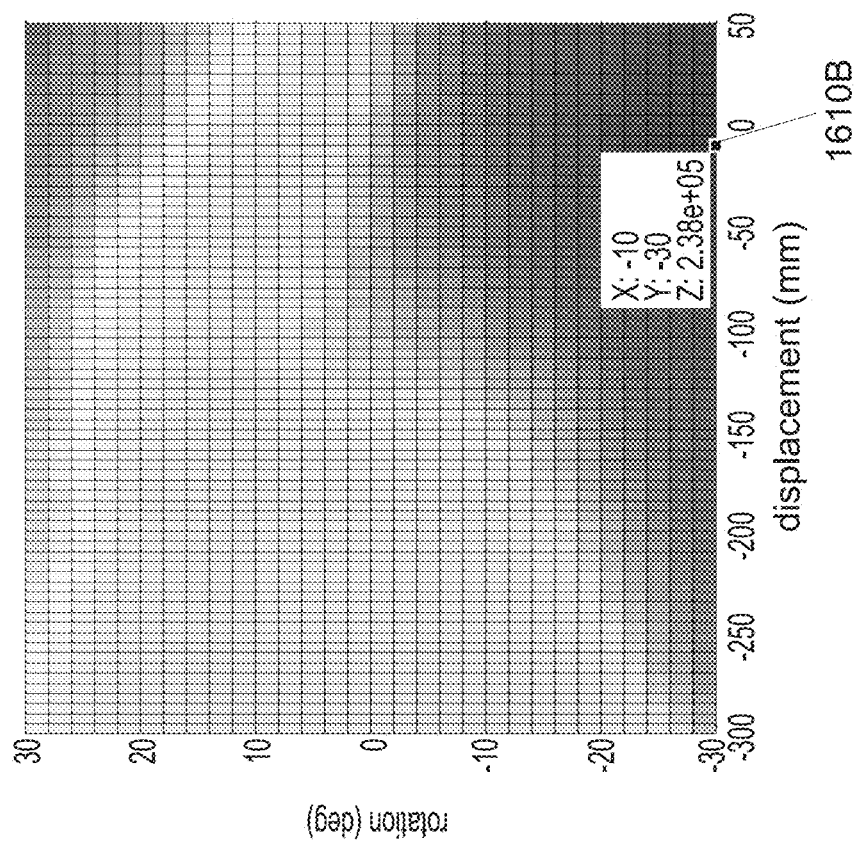

FIGS. 16A-B are based on one view of the detector relative to the patient, and FIGS. 16C-D are based on a different view.

FIGS. 16A and 16C graphically depict values experimentally measured by considering possible combinations in a 2D parameter space including distance on the x-axis (i.e., from the anchor point to the detector representing image scaling) and rotation along the y-axis (i.e., along the x-axis of the patient). The values were measured by iteratively scanning along the depicted parameter space. Sampling resolution is in 5 mm intervals for the distance parameter and 2 degrees for the angle parameter.

FIG. 16B (corresponding to FIG. 16A) and FIG. 16D (corresponding to FIG. 16C) depict a registered image including a fluoroscopic anatomical image 1602A/B, segmented vessels 1604A/B, and a left ventricle contour based on NM image data 1606 A/B.

Based on the measured values represented in FIG. 16A, the minimum set of points for the calculated cost function for the first view are identified as −185 millimeters (mm) and 18 degrees, as shown by number 1610A/B. Based on the cost function described with reference to FIG. 14, the corresponding calculated values are −170 mm and 17.4 degrees, indicating a high degree of accuracy using the cost function calculation method. Based on FIG. 16C, the minimum values of the other view are accurate: experimentally determined to be a translation of −10 mm and a rotation of −30 degrees, and calculated to have a value of a translation of −10 mm and a rotation of −30 degrees.

Figure 16E:
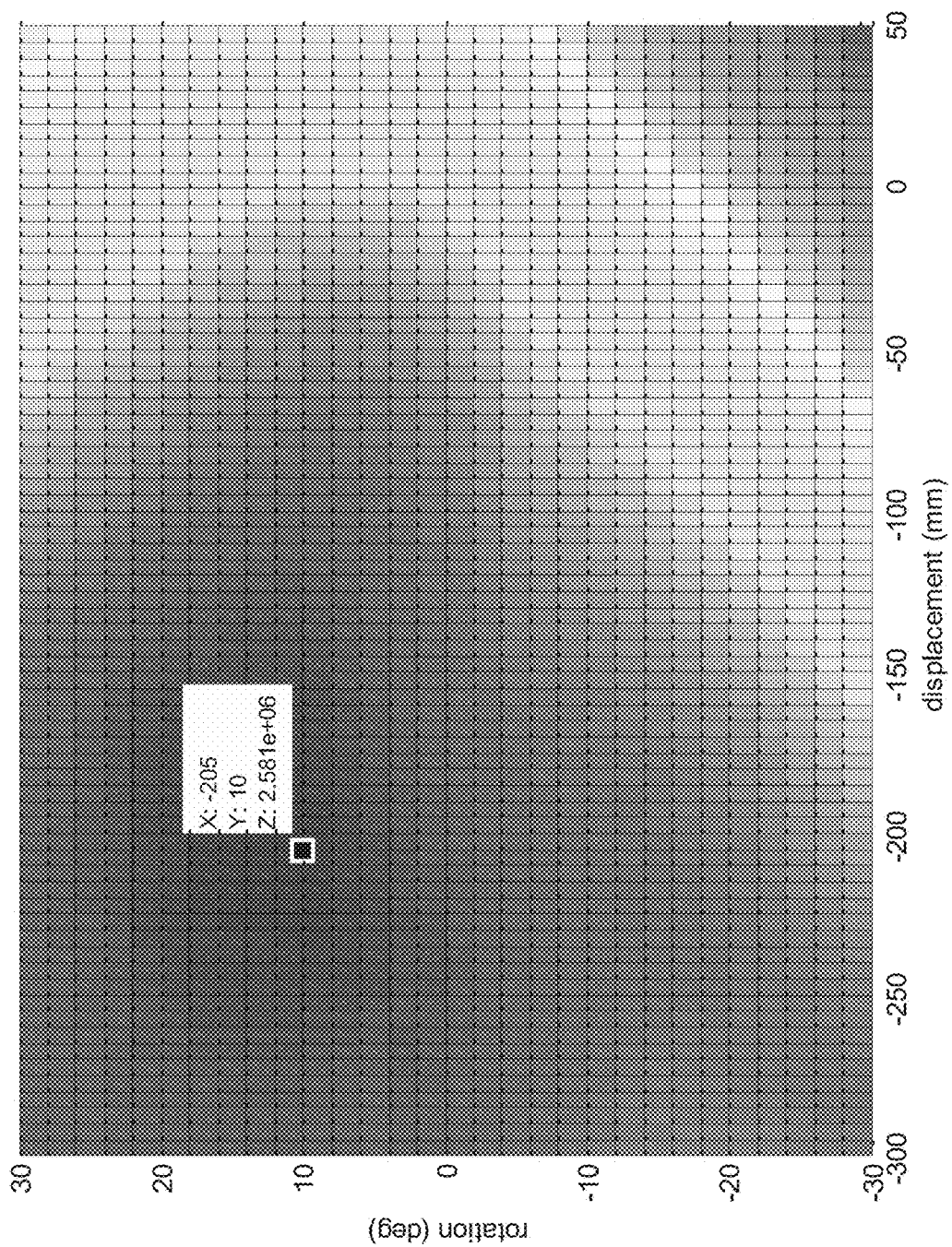

FIG. 16E is a graph depicting values experimentally measured for multiple views of the detector relative to the patient, such as the views used during the procedure. The global minimum for all frames is both experimentally measured and calculated to be a 10 degree rotation and −205 mm translation common for all the target frames.

Referring now back to FIG. 1, optionally, at 114, the registered image is displayed, optionally on a display 220, for example, a screen. The registered image includes the anatomical image and the NM contour, optionally based on different colors, which may be the original colors of the respective images (e.g., black and white anatomical image, and color coded NM image based on intensity).

The registered image may include an enhancement of the segmented vessels, for example, a marking, a label, a different color, and/or a different filling shade. In this manner, the user may visually identify any visually apparent un-segmented vessels.

The presented registered image may include only the segmented vessels and the NM contour. Alternatively, the presented image may include the anatomical image (the segmented vessels and background) and the NM contour. The user may toggle between the modes, for example, to help in identifying stenotic lesions and/or smaller vessels feeding the myocardium.

Figure 10:
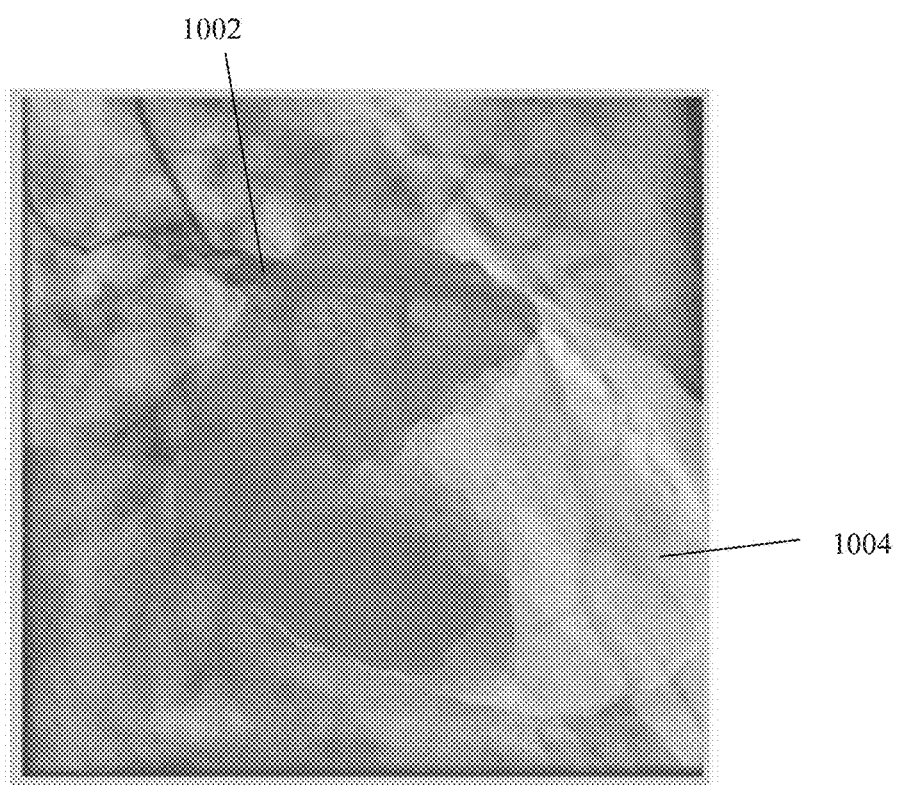
FIG. 10 is an exemplary registered image, in accordance with some embodiments of the present invention.

Reference is now made to FIG. 10, which is an exemplary registered image depicting a registration between a fluoroscopic image including a segmented heart vessel network 1002 and a contour image 1004 obtained from a NM device (i.e., a D-SPECT® machine), in accordance with some embodiments of the present invention.

Referring now back to FIG. 1, the registered image may be displayed as part of a user interface module 214E configured to display the registered image and allowing the user to interact with the registered image, for example, by processing signals received from a connected input element 222, for example, a touch screen, a mouse, a keypad, and a microphone coupled to voice recognition software.

Figure 11:
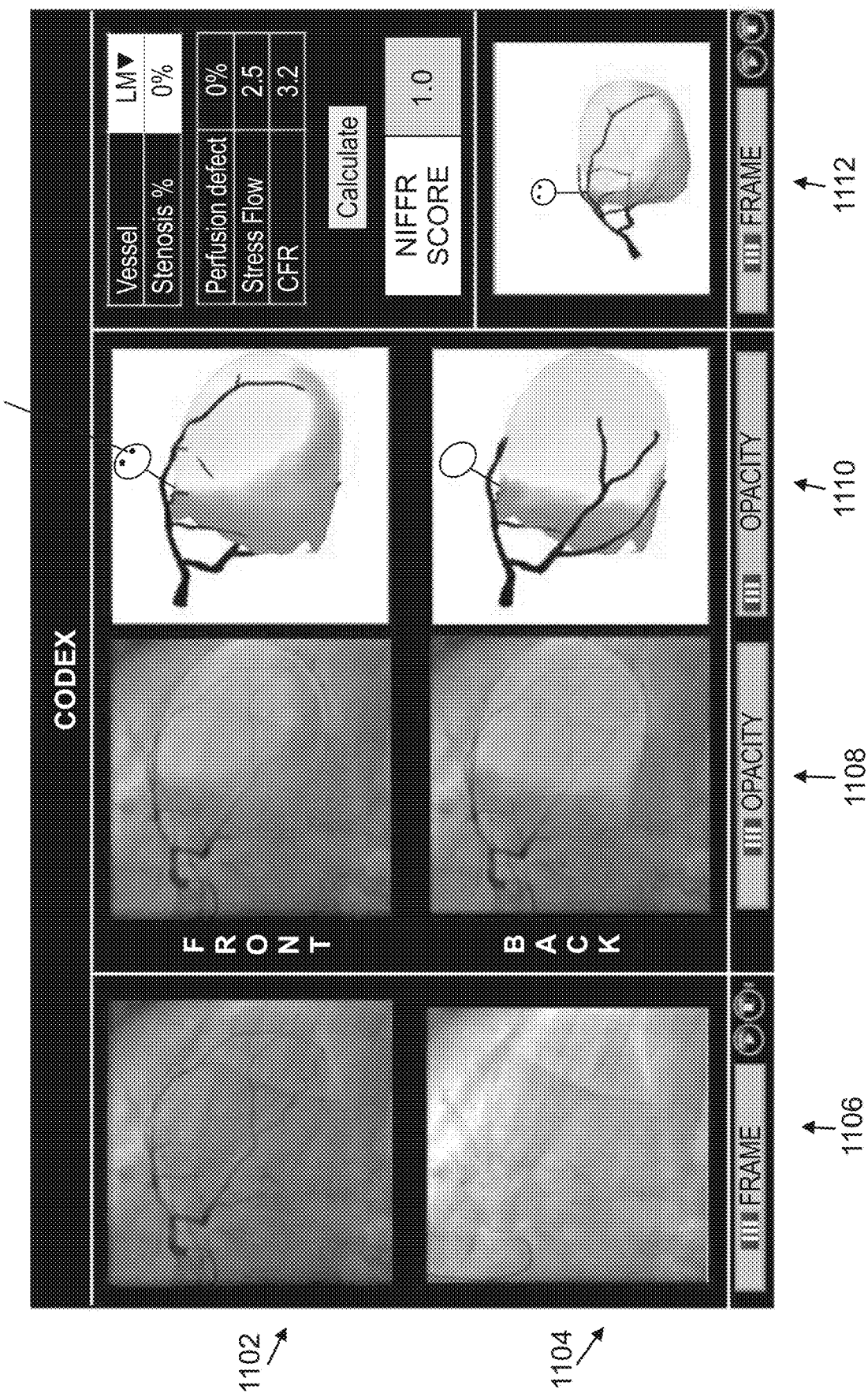
FIG. 11 is an exemplary user interface for displaying the registered image, in accordance with some embodiments of the present invention.

Reference is now made to FIG. 11, which is an exemplary user interface for displaying the registered image, in accordance with some embodiments of the present invention. The user interface may display images obtained from two (or more) different views. For example, a top row 1102 displays images acquired from a sensor (e.g., x-ray) positioned generally in front of the patient, and a bottom row 1104 displays images acquired from the sensor positioned generally behind the patient.

Different versions of the registered image may be displayed, for example, side by side in columns, or selected for single display. A first column 1106 may display the acquired anatomical image (e.g., fluoroscopic image). A second column 1108 may display the registered image that includes the anatomical image and the NM contour of the heart wall. A third column 1110 may display a version of the registered image that includes the segmented vessel network and the NM contour of the heart wall, without the remaining background features of the anatomical image. A fourth column 1112 may display an interactive platform for calculation of one or more physiological parameters based on the registered image, as described herein, for example, with reference to block 120 of FIG. 1. Optionally, the user interface is configured to allow the user to manually mark certain vessels (e.g., by a tag 1114) on the registered image. The physiological parameters may be calculated based on the marked vessel.

It is noted that display 220, input element 222 and user interface module 214E may be connected to processor 208, or to a different processor independent of processor 208. The independent processor may be, for example, a desktop computer, a remote server, a smartphone, a laptop computer, and a tablet computer. The independent processor may communicate with processor 208 to receive the registered images for local display and optional further processing as described herein, for example, through a network connection, output interface, and/or portable storage media.

Optionally, at 116, a manual user input indicative of one or more un-segmented vessels is received, for example, based on user interface 214E processing signals from input element 222. The user input represents vessels that should be part of the segmented vessel network, but that are not included as part of the segmented vessel network, for example, due to incorrect and/or incomplete segmentation.

The manual user input may include, for example, a click of a cursor on the un-segmented vessel(s), hovering with the cursor over the un-segmented vessel(s), the user manually touching his/her finger over the un-segmented vessel using a touch screen.

The manual user input may include a small region of the vessel (e.g., a click of the cursor or a press of the finger at one location of the vessel), multiple small regions, and/or a trace of the vessel (e.g., running the finger and/or cursor over most of the length of the vessel).

The user input may indicate one or more visible branch ends of the un-segmented vessel. The user input may indicate the largest vessel feeding the un-segmented vessels.

The user input may be received based on the registered image (including the anatomical image and the NM contour), or based on an image depicting the segmented vessel network, without the registered NM contour being displayed. The user input may be received after the execution of blocks 110 (correlation) and 112 (registration). Alternatively, the user input may be received after the execution of block 104 (identification of segmentation of vessel network) and block 117 (display of a preliminary image including an enhanced and/or marked segmentation of vessel network on the display, optionally using the user interface).

Optionally, at 118, the registered image (or the anatomical image before registration) is adapted to include the un-segmented vessels. Optionally, the segmented vessel network (e.g., as described with reference to blow 104) is adapted to incorporate the un-segmented vessel(s) as part of the segmented vessel network.

Each respective identified manual user input may act as seed point(s), which are grown towards the segmented vessel network, until the un-segmented vessels are included within the segmented vessel network.

The process of correlation (block 110), registration (block 112), and image display (block 114) may be repeated with the adapted segmented vessel network, to correlate and/or register the adapted registered vessel network with the NM contour to generate an adapted registered image incorporating the previously un-segmented vessels.

Figure 12:
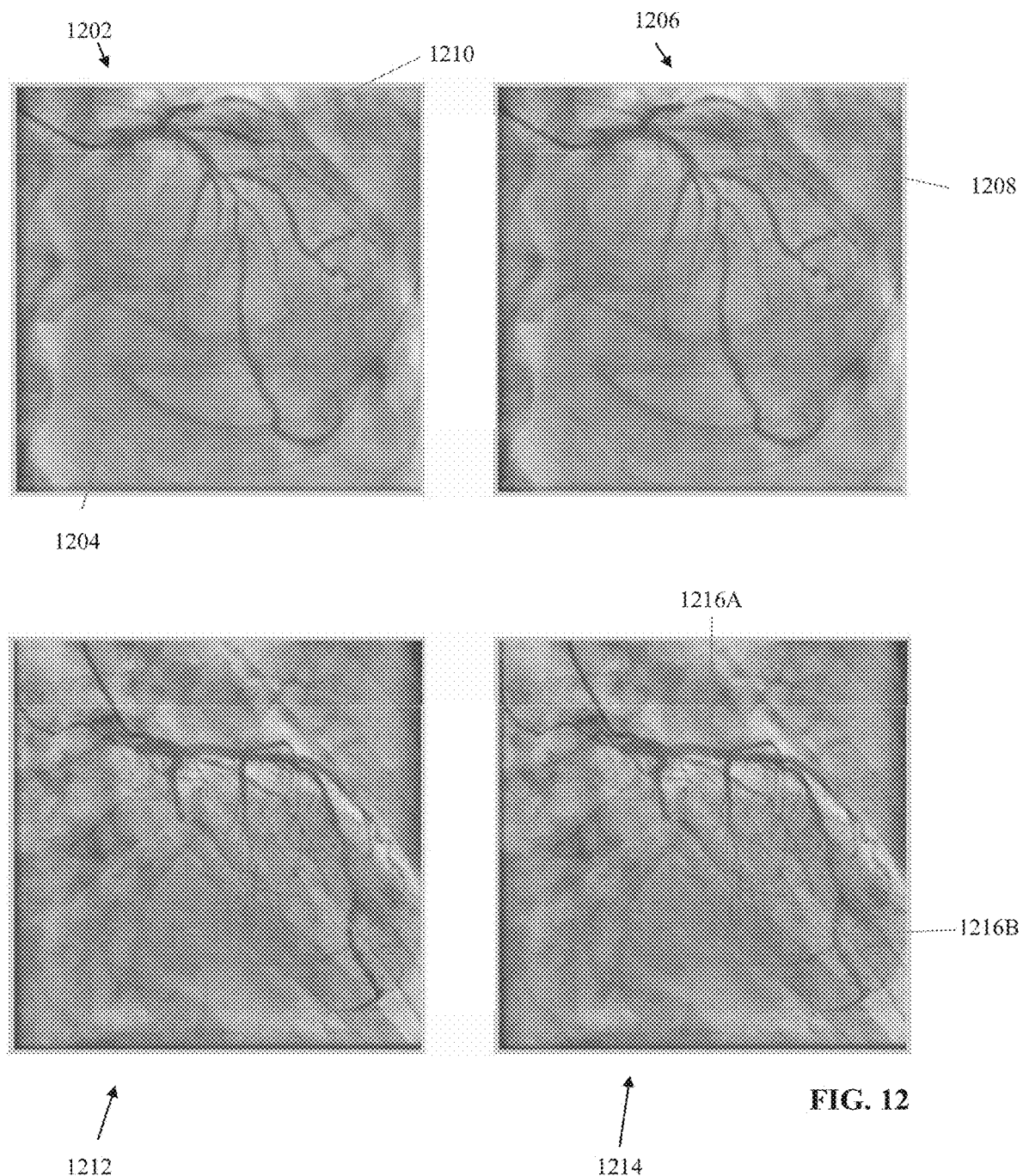
FIG. 12 includes before and after images depicting the inclusion of user identified vessels in the segmented vessel network, in accordance with some embodiments of the present invention.

Reference is now made to FIG. 12, which depicts anatomical images (fluoroscopic images of the heart) including a marked segmented vessel network (coronary arteries) before and after the manual user marking, in accordance with some embodiments of the present invention. For clarity, the images do not depict the registered NM contour, although the NM contour may be displayed as described herein.

Image 1202 is a fluoroscopic image of the left main coronary artery and branches thereof, including an enhanced (for visual distinction) segmented vessel network 1204. Image 1206 is the fluoroscopic version of image 1202 after adaptation to include an additional vessel region 1208 added to the segmented vessel network based on an identified user marking, as described herein. It is noted that vessel region 1210 corresponding to added vessel region 1208 is not part of segmented vessel network 1204 within image 1202 before the user marking.

Images 1212 and 1214 are another example of before and after images depicting the adaptation of the segmented vessel network based on user markings, to add additional un-segmented vessel regions. Image 1214 depicts enhanced vessel regions 1216A and 1218B added to the segmented vessel network.

Referring now back to FIG. 1, optionally, at 120, one or more calculations of physiological parameters are performed based on the displayed registered image, optionally based on a physiological parameter calculation module 214G configured to perform the calculations as described herein. The calculations may be guided by manual user input, automatic input, and/or automatically performed (e.g., for all identified vessels, or for certain vessels with lesions). The calculations may be performed based on image data represented by the manual user input on the registered image.

The calculations may help the operator evaluate the significance of a stenotic lesion or other vessel disease, which may help guide treatment. Certain stenotic lesions may look bad on anatomical images, but not have a significant effect on the amount of blood supplied to the myocardium of the heart. In contrast, certain stenotic lesions may look fine or not significant on anatomical images, but may have a drastic effect in reducing blood to the myocardium.

The registered image helps correlate calculations defining structure with functional performance calculations, which may aid in understanding the functional effects of structural lesions.

Optionally, a manual user input indicative of a stenotic lesion within a certain vessel of the network of segmented vessels of the displayed registered image is identified, for example, the user manually marking the stenosis. Alternatively or additionally, automatic input of an automatically identified stenotic lesion is provided, for example, based on an analysis of the diameter of the vessel along the segmented vessel. The percent stenosis may be calculated for the stenotic lesion based on the image, for example, from the anatomical image itself.

Alternatively or additionally, a manual user input indicative of one or more vessels for calculation of related functional parameters is identified. Alternatively or additionally, automatic input of an automatically identified region is provided, for example, based on identification of the segmented vessel extremity corresponding to the stenosis. The manual input may include selection and/or identification of end regions and/or branches of the vessel. The vessel may have a stenotic lesion or other structure vessel disease. The vessel may be the same vessel used for calculation of the percent stenosis. The functional parameters may be calculated based on the NM image data correlated with the user selected vessel. The NM image data may include the portions of the myocardium that are supplied with blood by the selected vessel.

Additional data may be provided as input for the calculations, for example, data based on patient medical history, such as demographics, and cardiac risk factors.

Exemplary functional parameters that may be calculated include one or more of:

perfusion defect for the heart muscle fed by the selected vessel;

stress flow based on the selected vessel;

coronary flow reserve (CFR) based on the selected vessel (CFR may be calculated as the ratio between stress flow and rest flow); and non-invasive Fractional Flow Reserve (NIFFR) score.

Figure 13:
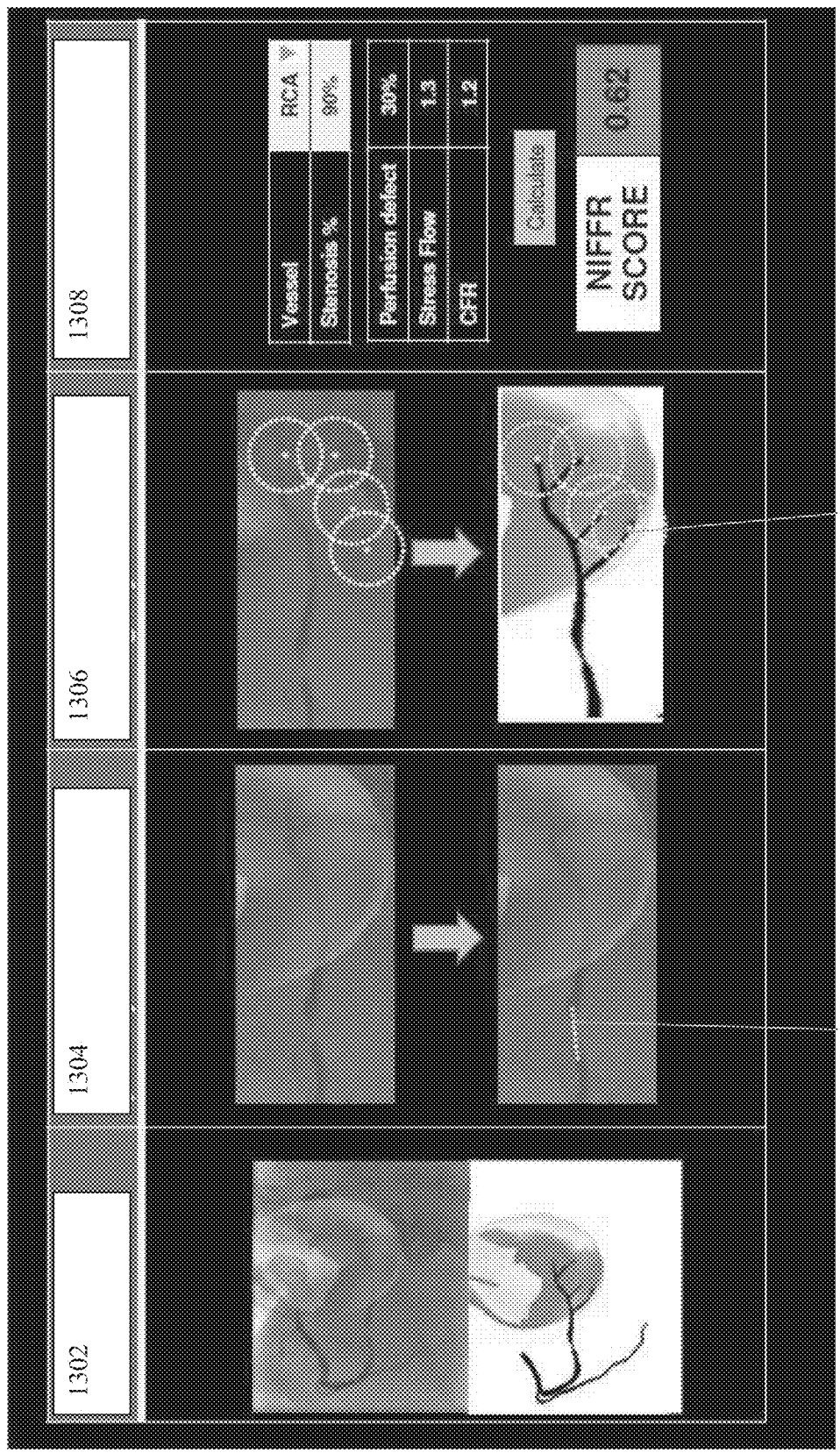
FIG. 13 is an exemplary user interface for calculation of one or more physiological parameters based on the registered image, in accordance with some embodiments of the present invention.

Reference is now made to FIG. 13, which is an image of an exemplary user interface configured to accept user input and calculate one or more functional parameters based on the registered image, in accordance with some embodiments of the present invention. Columns 1302-1308 may be displayed sequentially as the user provides input, or simultaneously, such as side by side.

At column 1302, the user interface is configured to allow the user to select a desired frame as a basis for calculation of the physiological parameters, for example, a frame depicting a segmented vessel region with a stenotic lesion.

At column 1304, a manual marking from the user defining the stenotic area is identified, for example, a manually placed marking 1310 on the displayed registered image. Relevant physiological parameters are calculated based on the identified stenosis.

At column 1306, one or more manual markings from the user representing vessel ends feeding the myocardium are identified, for example, based on one or more manually placed markings 1312 on the displayed registered image. Relevant physiological parameters are calculated based on the identified vessel ends.

At column 1308, the physiological parameters are calculated based on the identified user markings, as described herein. The vessel may be automatically selected by the user interface, or manually by the user.

Referring now back to FIG. 1, optionally at 122, an additional anatomical image acquisition session is performed. For example, the anatomical imaging modality sensor is re-positioned relative to the patient, contrast is injected into different vessels or lumens, or the images using the same sensor position and similar contrast injection is repeated (e.g., to try and improve image quality, after adjusting radiation dose, or adjustment of other imaging factors).

In this manner, blocks 102-114 may be dynamically and/or iteratively repeated during a diagnostic and/or treatment sessions, for example, during a cardiac catheterization procedure.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical imaging modalities and nuclear medicine imaging modalities will be developed and the scope of the terms anatomical images and NM images are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for registration of intravital anatomical imaging modality image data and nuclear medicine image data of a heart of a patient, comprising:

obtaining anatomical two dimensional (2D) image data captured by at least one of a fluoroscopy machine and a 2D x-ray machine, the anatomical 2D image data including a heart of a patient;

wherein the anatomical 2D image data includes at least two 2D anatomical images captured from two or more differing viewing angles of the heart of the patient by at least one of the fluoroscopy machine and the 2D x-ray machine;

obtaining at least one three dimensional (3D) nuclear medicine image data outputted by a nuclear medicine imaging modality, the at least one nuclear medicine image data including the heart of the patient;

identifying a segmentation of a network of vessels of the heart in the 2D anatomical image data;

identifying a contour of at least part of the heart in the at least one 3D nuclear medicine image data, the contour including at least one muscle wall border of the heart;

correlating the segmentation obtained from 2D image data captured from two or more different viewing angles by the at least one of a fluoroscopy machine and a 2D x-ray machine, and the contour obtained from the nuclear medicine image data;

registering the correlated segmentation obtained from the 2D image data captured from two or more different viewing angles by the at least one of a fluoroscopy machine and a 2D x-ray machine, and the correlated contour obtained from the 3D nuclear medicine image data to form a registered image of the 2D anatomical image data and the at least one 3D nuclear medicine image data; and
providing the registered image for display.

2. The method of claim 1, further comprising:
retrieving the anatomical image data from a sequence of images including at least one previous image; and
identifying the segmentation of the anatomical image data based on at least one seed point derived from a previous segmentation of the at least one previous image from the sequence of images.

3. The method of claim 2, wherein the sequence of images is selected based on a range of images including a first frame prior to injection of contrast material into the network of vessels, and including a last frame of the contrast enhanced network of vessels prior to washing away of the contrast material from the network of vessels.

4. The method of claim 3, wherein the range of images are automatically selected based on the first frame denoted by an initial rise in a parameter representing size of a connected segmented component in each image, and based on the last frame denoted by a fall from a plateau of the parameter.

5. The method of claim 3, wherein the identifying the segmentation of the network of vessels is performed for at least two of the images within the range of images, and the at least two of the images are correlated with the same at least one 3D nuclear medicine image data.

6. The method of claim 3, further comprising connecting unconnected segmented vessels to form a single connected segmented component when the unconnected segmented vessels have a distance from the single connected segmented component that is less than a predefined threshold, and wherein unconnected segmented vessels that have the distance larger than the predefined threshold are excluded.

7. The method of claim 1, further comprising:
identifying a manual user input or automatic input indicative of a stenotic lesion within a certain vessel of the network of segmented vessels of the registered image;
identifying a manual user input or automatic input indicative of at least one end region of the certain vessel feeding the heart wall muscle of the registered image; and
calculating at least one physiological parameter based on correlated 3D nuclear medicine imaging data of the portion of the heart wall associated with the certain vessel;
wherein the at least one physiological parameter is selected from the group consisting of: perfusion of heart muscle fed by the certain vessel, perfusion defect severity or extent for heart muscle fed by the certain vessel, stress flow based on the certain vessel, coronary flow reserve based on the certain vessel, and NIFFR score.

8. The method of claim 1, further comprising:
identifying at least one manual user input indicative of at least one un-segmented vessel based on the registered image; and
adapting the registered image to include the at least one un-segmented vessel as part of the segmented vessel network, based on the at least one manual user input acting as at least one seed point grown towards the segmented vessel network.

9. The method of claim 1, further comprising:
obtaining another anatomical image data including contrast in a lumen of a left ventricle of the heart, outputted by the anatomical intravital imaging modality;
identifying at least one anatomical structure of the left ventricle in the another at anatomical image data;
correlating between the contour and the at least one anatomical structure of the left ventricle; and
correlating between the contour and the segmented vessel network based on the correlation between the contour and the at least one anatomical structure of the left ventricle.

10. The method of claim 1, wherein the registering is based on a projection of a generic angiographic model of heart vessels onto a 2D plane corresponding to a plane of the anatomical image of the segmented vessel network.

11. The method of claim 1, wherein obtaining comprises obtaining at least two sets of the anatomical image data based on at least two different views of the anatomical intravital imaging modality relative to the patient, and further comprising registering between the at least two sets based on relative respective positions of the anatomical imaging modality during the at least two different views.

12. The method of claim 11, further comprising:
generating a three dimensional (3D) model of vessels based on the segmented vessels of the registered at least two sets; and
correlating and registering the contour based on the 3D model.

13. The method of claim 1, further comprising:
generating a mesh projection of the contour;
generating an ellipsoid generally encompassing the segmented network of vessels; and
correlating the mesh projection with the ellipsoid.

14. The method of claim 1, further comprising:
identifying a silhouette of the heart wall border visualized in the anatomical image data;
correlating between the contour and the silhouette; and
correlating between the contour and the segmentation based on the correlation between the contour and the silhouette.

15. The method of claim 1, further comprising:
identifying a location of an apex of the heart within the anatomical image data;
correlating between the contour and the apex; and
correlating between the contour and the segmentation based on the correlation between the contour and the apex.

16. The method of claim 1, further comprising:
identifying the network of vessels within the anatomical image data;
generating a vessel image based on the identified network of vessels;
selecting at least one seed point for the segmentation based on the vessel image such that the at least one seed point is located within the identified network of vessels;
creating a homogeneity map to identify homogenous regions in the anatomical image data; and
segmenting the anatomical image data based on the homogeneity map, the at least one seed point and the anatomical image data based on growing the seed points within the anatomical image data guided by the homogeneity map.

17. The method of claim 1, wherein registering comprises constraining the segmented vessel network within the contour by performing at least one of rotation and scaling of the contour based on obtaining minimum values calculated from a predefined cost function, and further comprising selecting an anchor point for the segmented vessels to lock the segmented vessels in two dimensions to prevent translation of the segmented vessels and to allow scaling based on motion along an imaginary line connecting the anchor point and a detector.

18. The method of claim 1, wherein the at least two 2D anatomical images captured from two or more different viewing angles of the heart are separated by at least 20 degrees.

19. A computer implemented method for adapting a registration between 2D intravital anatomical imaging modality image data and 3D nuclear medicine image data of a heart of a patient, comprising:

obtaining a registered image generated between 2D intravital anatomical imaging modality image data captured by at least one of a fluoroscopy machine and a 2D x-ray machine and 3D nuclear medicine image data of a heart of a patient, the registered image including a segmentation of a network of vessels of the heart, wherein the anatomical 2D image data includes at least two 2D anatomical images captured from two or more different viewing angles of the heart of the patient by at least one of the fluoroscopy machine and the 2D x-ray machine, wherein the registered image is computed by correlating segmentation of the network of vessels of the heart obtained from the 2D images captured from two or more different viewing angles by the at least one of a fluoroscopy machine and a 2D x-ray machine, and a correlated contour obtained from the 3D nuclear medicine image data;

identifying at least one manual user input indicative of at least one un-segmented vessel within the registered image; and adapting the registered image to include the at least one un-segmented vessel as part of the segmented vessel network, based on the at least one manual user input acting as at least one seed point grown towards the segmented vessel network.

20. A system for registration of 2D intravital anatomical imaging modality image data and 3D nuclear medicine image data of a heart of a patient, comprising:

a central server comprising:

an anatomical interface configured to obtain 2D anatomical image data captured by at least one of a fluoroscopy machine and a 2D x-ray machine, the 2D anatomical image data including a heart of a patient;

wherein the anatomical 2D image data includes at least two 2D anatomical images captured from two or more differing viewing angles of the heart of the patient by at least one of the fluoroscopy machine and the 2D x-ray machine;

a nuclear medicine interface configured to obtain at least one 3D nuclear medicine image data outputted by a nuclear medicine imaging modality, the at least one 3D nuclear medicine image including the heart of the patient;

a hardware processor;

a memory in communication with the processor, the memory having stored thereon code instruction for execution by the processor, including:

code to identify a segmentation of a network of vessels of the heart in the 2D anatomical image data;

code to identify a contour of at least part of the heart in the at least one 3D nuclear medicine image, the contour including at least one muscle wall border of the heart;

code to correlate between the segmentation obtained from the 2D images captured from two or more different viewing angles by the at least one of a fluoroscopy machine and a 2D x-ray machine, and the contour obtained from the 3D nuclear medicine image data;

code to register the correlated segmentation obtained from the 2D images captured from two or more different viewing angles by the at least one of a fluoroscopy machine and a 2D x-ray machine, and the correlated contour obtained from the 3D nuclear medicine image data to form a registered image; and an output interface configured to provide the registered image for display.

21. The system of claim 20, wherein the 3D nuclear medicine imaging modality includes a D-SPECT machine.

* * * * *

UNITED STATES PATENT AND TRADEMARK OFFICE
CERTIFICATE OF CORRECTION

| | | |
|---|---|---|
| PATENT NO. | : 11,232,577 B2 | Page 1 of 1 |
| APPLICATION NO. | : 15/546377 | |
| DATED | : January 25, 2022 | |
| INVENTOR(S) | : Yoel Zilberstien | |

It is certified that error appears in the above-identified patent and that said Letters Patent is hereby corrected as shown below:

On the Title Page

Item (73) Assignee, "Speetrum Dynamics Medical Limited" should be changed to -- Spectrum Dynamics Medical Limited --

Signed and Sealed this
Twenty-sixth Day of April, 2022

Katherine Kelly Vidal
*Director of the United States Patent and Trademark Office*